(12) United States Patent
Liu et al.

(10) Patent No.: US 12,357,831 B2
(45) Date of Patent: Jul. 15, 2025

(54) VOLTAGE REGULATING MODULE AND IMPLANTABLE NERVE STIMULATION SYSTEM

(71) Applicant: SCENERAY CO., LTD., Jiangsu (CN)

(72) Inventors: Bin Liu, Jiangsu (CN); Jinghua Chen, Jiangsu (CN); Weiran Zhu, Jiangsu (CN)

(73) Assignee: SCENERAY CO., LTD., Jiangsu (CN)

( * ) Notice: Subject to any disclaimer, the term of this patent is extended or adjusted under 35 U.S.C. 154(b) by 564 days.

(21) Appl. No.: 17/771,849

(22) PCT Filed: Nov. 28, 2019

(86) PCT No.: PCT/CN2019/121538
§ 371 (c)(1),
(2) Date: Apr. 26, 2022

(87) PCT Pub. No.: WO2021/082156
PCT Pub. Date: May 6, 2021

(65) Prior Publication Data
US 2022/0370807 A1    Nov. 24, 2022

(30) Foreign Application Priority Data
Nov. 1, 2019    (CN) .......................... 201911060243.3

(51) Int. Cl.
*A61N 1/36*    (2006.01)
*A61N 1/05*    (2006.01)
*H02M 3/07*    (2006.01)

(52) U.S. Cl.
CPC ....... *A61N 1/36153* (2013.01); *A61N 1/0551* (2013.01); *A61N 1/36125* (2013.01); *H02M 3/073* (2013.01)

(58) Field of Classification Search
CPC ............ H03K 17/0828; H03K 17/168; H03K 2017/0806; H03K 2217/0027;
(Continued)

(56) References Cited

U.S. PATENT DOCUMENTS

| 4,451,743 A | 5/1984 | Suzuki et al. |
| 9,312,831 B2 * | 4/2016 | Nestler .................. G10K 15/00 |

(Continued)

FOREIGN PATENT DOCUMENTS

| CN | 1376327 A | 10/2002 |
| CN | 104868706 A | 8/2015 |

(Continued)

OTHER PUBLICATIONS

Extended European Search Report in Application No. 19950638.7 dated Sep. 15, 2023, 6 pages.

(Continued)

*Primary Examiner* — Jung Kim
(74) *Attorney, Agent, or Firm* — ArentFox Schiff LLP; Joseph M. Maraia; Marlo Schepper Grolnic

(57) ABSTRACT

A voltage regulating module includes a fine regulating charge pump and a voltage-multiplying charge pump. The first output voltage of the fine regulating charge pump is $V_1=m*V_0$, a second output voltage of the voltage-multiplying charge pump is $V_2=n*V_0$, and a total output voltage of the voltage regulating module $V=V_1+V_2$. $V_0$ is an input voltage, a value of m ranges from 0 to 1, and n is an integer greater than or equal to 1.

16 Claims, 15 Drawing Sheets

(58) Field of Classification Search
CPC ......... G11C 5/145; G11C 5/146; G11C 5/147; G11C 5/148; H02M 3/07; H02M 3/071; H02M 3/072; H02M 3/073; H02M 3/075; H02M 3/076; H02M 3/077
See application file for complete search history.

(56) References Cited

U.S. PATENT DOCUMENTS

| | | |
|---|---|---|
| 2002/0068957 A1 | 6/2002 | Wolfe et al. |
| 2010/0114252 A1 | 5/2010 | Torgerson |
| 2012/0197330 A1 | 8/2012 | Crutchfield et al. |

FOREIGN PATENT DOCUMENTS

| | | |
|---|---|---|
| CN | 105879219 A | 8/2016 |
| CN | 107185109 A | 9/2017 |
| CN | 107485785 A | 12/2017 |
| CN | 110336348 A | 10/2019 |
| CN | 211097046 U | 7/2020 |
| DE | 102006046387 A1 | 4/2008 |

OTHER PUBLICATIONS

Office Action for related CN Application No. 201911060243.3 dated Jun. 21, 2024 (17 pgs).
International Search Report for related Application No. PCT/CN2019/121538 mailed Jul. 28, 2020.

* cited by examiner

VOLTAGE REGULATING MODULE AND IMPLANTABLE NERVE STIMULATION SYSTEM

CROSS-REFERENCE TO RELATED APPLICATIONS

This is a national stage application filed under 37 U.S.C. 371 based on International Patent Application No. PCT/CN2019/121538, filed Nov. 28, 2019, which claims priority to a Chinese patent application No. 201911060243.3 filed on Nov. 1, 2019, disclosures of which are incorporated herein by reference in its entirety.

TECHNICAL FIELD

The present disclosure relates to the field of implantable medical treatment and, in particular, to a voltage regulating module and an implantable nerve stimulation system.

BACKGROUND

Implantable medical system has been more and more widely used in medical clinic in recent years. It usually includes an implantable nerve stimulation system (including a deep brain stimulation system (DBS), an implantable cortical stimulation system (CNS), an implantable spinal cord stimulation system (SCS), an implantable sacral nerve stimulation system (SNS), an implantable vagus nerve stimulation system (VNS) and the like), an implantable heart stimulation system (known as a cardiac pacemaker), an implantable drug delivery system (DDS) and the like.

In the implantable medical system, a nerve stimulation system performs chronic electrical stimulation on target nerves so as to effectively control symptoms of functional neurological diseases and psychosis.

The frequency and amplitude of the target neural signal can reflect the condition of the nerve disease. By reading the target neural signal, the condition of the disease can be determined and the optimal treatment mode can be adopted, the therapeutic effect of the nerve stimulation system can also be objectively determined.

In practice, the stimulation amplitudes required by different individuals are quite different, the range of the stimulation amplitude may range from 0.1V to 14V. Since the battery can only provide a power supply voltage of 3.6V, and the actual output stimulation amplitude is an integer multiple of the power supply voltage, the actual output stimulation amplitude is generally different from the required stimulation amplitude, so that the stimulation amplitude in the existing art cannot be finely adjusted, thereby causing the waste of the power consumption.

SUMMARY

The object of the present disclosure is to provide a voltage regulating module and an implantable nerve stimulation system.

In order to achieve the above propose, an embodiment of the present disclosure provides a voltage regulating module. The voltage regulating module includes a fine regulating charge pump and a voltage-multiplying charge pump. A first output voltage of the fine regulating charge pump is $V_1=m*V_0$, a second output voltage of the voltage-multiplying charge pump is $V_2=n*V_0$, and a total output voltage of the voltage regulating module is $V=V_1+V_2$, where $V_0$ is an input voltage, a value of m ranges from 0 to 1, and n is an integer greater than or equal to 1.

As a further improvement of one embodiment of the present disclosure, an input terminal of the fine regulating charge pump is connected to the input voltage, an input terminal of the voltage-multiplying charge pump is connected to the input voltage, and the fine regulating charge pump and the voltage-multiplying charge pump are connected through an intermediate switch.

As a further improvement of one embodiment of the present disclosure, the fine regulating charge pump includes: several fine regulating charge pump basic units, each fine regulating charge pump basic unit includes a fine regulating charge branch, a fine regulating discharge branch, several fine regulating capacitors located in the fine regulating charge branch and the fine regulating discharge branch, and several fine regulating switches. The fine regulating charge branch is configured to charge the several fine regulating capacitors, the fine regulating discharge branch is configured to output an intermediate output voltage, the intermediate output voltage serves as a first output voltage or is output to another adjacent fine regulating charge pump basic unit, and the fine regulating charge branch and the fine regulating discharge branch are controlled by the several fine regulating switches to output different intermediate output voltages.

As a further improvement of one embodiment of the present disclosure, each fine regulating charge pump basic unit further includes a series branch connected in series with the fine regulating discharge branch, the series branch includes at least one series input terminal and a series switch for controlling opening and closing of the at least one series input terminal, the at least one series input terminal is configured to ground or connect the intermediate output voltage of another fine regulating charge pump basic unit to output a series voltage, in a case where the fine regulating discharge branch and the series branch are turned on, the first output voltage is a sum of the intermediate output voltage of the fine regulating discharge branch and the series voltage.

As a further improvement of one embodiment of the present disclosure, each fine regulating charge pump basic unit includes two fine regulating capacitors, in a case where the fine regulating charge branch is turned on, the input voltage or the intermediate output voltage charges the two fine regulating capacitors connected in series, and then in a case where the fine regulating discharge branch and the series branch are turned on, the two fine regulating capacitors are connected in parallel, the first output voltage is a sum of voltages at both ends of the fine regulating capacitors and the series voltage.

As a further improvement of one embodiment of the present disclosure, the fine regulating charge pump includes a first fine regulating charge pump basic unit, a second fine regulating charge pump basic unit, a third fine regulating charge pump basic unit and a fourth fine regulating charge pump basic unit which are connected in sequence. The first fine regulating charge pump basic unit includes a first series branch, a first fine regulating charge branch, a first fine regulating discharge branch, two first fine regulating capacitors located in the first fine regulating charge branch and the first fine regulating discharge branch, and several first fine regulating switches, and the first fine regulating charge branch is connected to the input voltage, the first fine regulating discharge branch outputs a first intermediate output voltage; the second fine regulating charge pump basic unit includes a second series branch, a second fine regulating charge branch, a second fine regulating discharge branch, two second fine regulating capacitors located in the second fine regulating charge branch and the second fine regulating discharge branch, and several second fine regulating switches, the second fine regulating charge branch is connected to the first intermediate output voltage, and the second fine regulating discharge branch outputs a second intermediate output voltage; the third fine regulating charge pump basic unit includes a third series branch, a third fine regulating charge branch, a third fine regulating discharge branch two third fine regulating capacitors located in the third fine regulating charge branch and the third fine regulating discharge branch, and several third fine regulating switches, the third fine regulating charge branch is connected to the second intermediate output voltage, and the third fine regulating discharge branch outputs a third intermediate output voltage; and the fourth fine regulating charge pump basic unit includes a fourth series branch, a fourth fine regulating charge branch, a fourth fine regulating discharge branch, two fourth fine regulating capacitors located in the fourth fine regulating charge branch and the fourth fine regulating discharge branch, and several fourth fine regulating switches, the fourth fine regulating charge branch is connected to the third intermediate output voltage, and the fourth fine regulating discharge branch outputs a fourth intermediate output voltage, and where the first series branch is grounded or connected to one of the second intermediate output voltage, the third intermediate output voltage and the fourth intermediate output voltage, the second series branch is grounded or connected to one of the third intermediate output voltage and the fourth intermediate output voltage, the third series branch is grounded or connected to the fourth intermediate output voltage, and the fourth series branch is grounded.

As a further improvement of one embodiment of the present disclosure, the voltage-multiplying charge pump includes: several voltage-multiplying charge branches, several voltage-multiplying discharge branches, several voltage-multiplying capacitors located in the several voltage-multiplying charge branches and the several voltage-multiplying discharge branches, and several voltage-multiplying charge switches, where the several voltage-multiplying charge branch is configured to charge the several voltage-multiplying capacitors, the several voltage-multiplying discharge branches are configured to output the second output voltage, and the several voltage-multiplying charge branches and the several voltage-multiplying discharge branches are controlled by the several voltage-multiplying switches to output different second output voltages.

As a further improvement of one embodiment of the present disclosure, the several voltage-multiplying charge branches include a first voltage-multiplying charge branch, a second voltage-multiplying charge branch, and a third voltage-multiplying charge branch; the several voltage-multiplying discharge branches include a first voltage-multiplying discharge branch, a second voltage-multiplying discharge branch, and a third voltage-multiplying discharge branch; and the several voltage-multiplying capacitors include a first voltage-multiplying capacitor, a second voltage-multiplying capacitor, and a third voltage-multiplying capacitor. The first voltage-multiplying charge branch is connected to the input voltage and the first voltage-multiplying capacitor, the second voltage-multiplying charge branch is connected to the input voltage and the second voltage-multiplying capacitor, and the third voltage-multiplying charge branch is connected to the input voltage and the third voltage-multiplying capacitor, the first voltage-multiplying discharge branch is connected to the first voltage-multiplying capacitor, the second voltage-multiplying discharge branch is connected to the first voltage-multiplying capacitor and the second voltage-multiplying capacitor in series, and the third voltage-multiplying discharge branch is connected to the first voltage-multiplying capacitor, the second voltage-multiplying capacitor and the third voltage-multiplying capacitor in series. In a case where the first voltage-multiplying charge branch is turned on and then the first voltage-multiplying discharge branch is turned on, the second output voltage is $V_2=V_0$, in a case where the first voltage-multiplying charge branch and the second voltage-multiplying charge branch are turned on and then the second voltage-multiplying discharge branch is turned on, the second output voltage is $V_2=2*V_0$, and in a case where the first voltage-multiplying charge branch, the second voltage-multiplying charge branch and the third voltage-multiplying charge branch are turned on and then the third voltage-multiplying discharge branch is turned on, the second output voltage is $V_2=3*V_0$.

As a further improvement of one embodiment of the present disclosure, the voltage regulating module also includes a comparator. Two input ends of the comparator are respectively connected to a preset voltage and a total output voltage, the total output voltage is controlled by several switches, and in a case where the total output voltage is not greater than the preset voltage, the comparator outputs a control signal to improve a working frequency of the several switches.

In order to achieve the above propose, one embodiment of the present disclosure provides an implantable nerve stimulation system including a terminal device and a stimulation electrode. The terminal device includes the voltage regulating module of any one of the above technical solutions, and the voltage regulating module is configured to output a total output voltage to control an electrical stimulation amplitude of the stimulation electrode.

Compared with the existing art, the present disclosure has following beneficial effects. In one embodiment of the present disclosure, the combination mode of the fine regulating charge pump and the voltage-multiplying charge pump outputs a large-scale finely-regulatable total output voltage, so that the actual total output voltage V is close to a required stimulation amplitude as much as possible, thereby greatly reducing power consumption.

DETAILED DESCRIPTION

The present disclosure will be described below in detail with reference to the specific embodiments illustrated in the accompanying drawings. However, these embodiments are not intended to limit the present disclosure. Any changes in structures, methods or functions made by those skilled in the art based on these embodiments are within the scope of the present disclosure.

Figure 1:
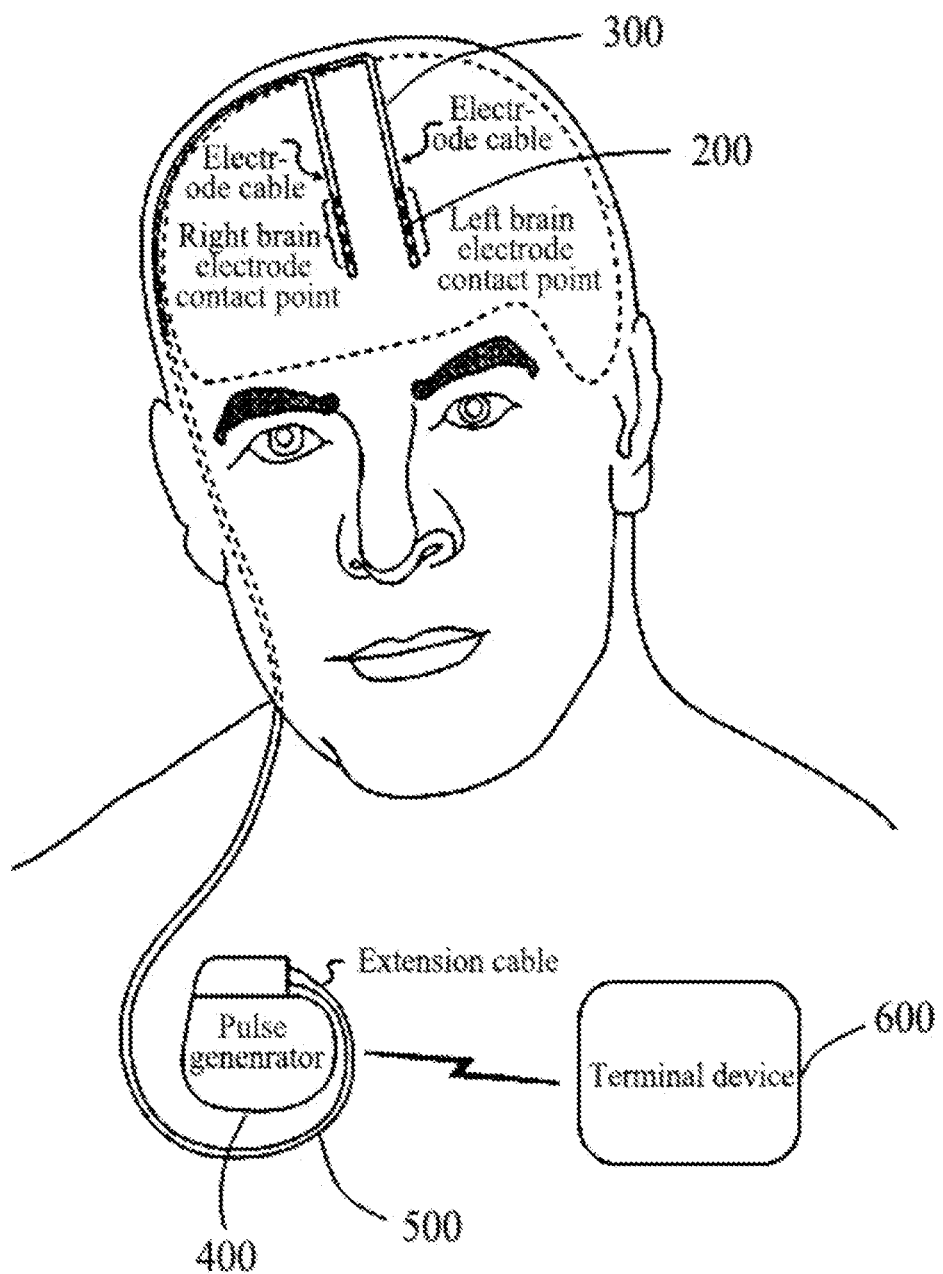
FIG. 1 is a schematic diagram of an implantable nerve stimulation system according to an embodiment of the present disclosure.

Referring to FIG. 1, an embodiment of the present disclosure provides an implantable nerve stimulation system.

The implantable nerve stimulation system typically includes the following components: several stimulation electrodes 200 (left brain electrodes and right brain electrodes are taken as examples here), an electrode cable 300, an extension cable 500, a pulse generator 400 and a terminal device 600.

A deep brain stimulation system (DBS) is taken as an example, the pulse generator 400 conducts an electrical pulse to the subthalamic Nucleus (STN) of the brain through the extension cable 500, the electrode cable 300 and the stimulation electrode 200 to achieve the purpose of treating diseases such as Parkinson's disease.

The terminal device 600 takes a program-controlled instrument as an example. The program-controlled instrument is configured to adjust various stimulation parameters of the pulse generator 400. The stimulation parameters include a pulse amplitude, a pulse width, a pulse frequency and the like. It is understood that the terminal device 600 may be other devices, such as a display device or the like, which may be determined according to the actual situation.

Figure 2:
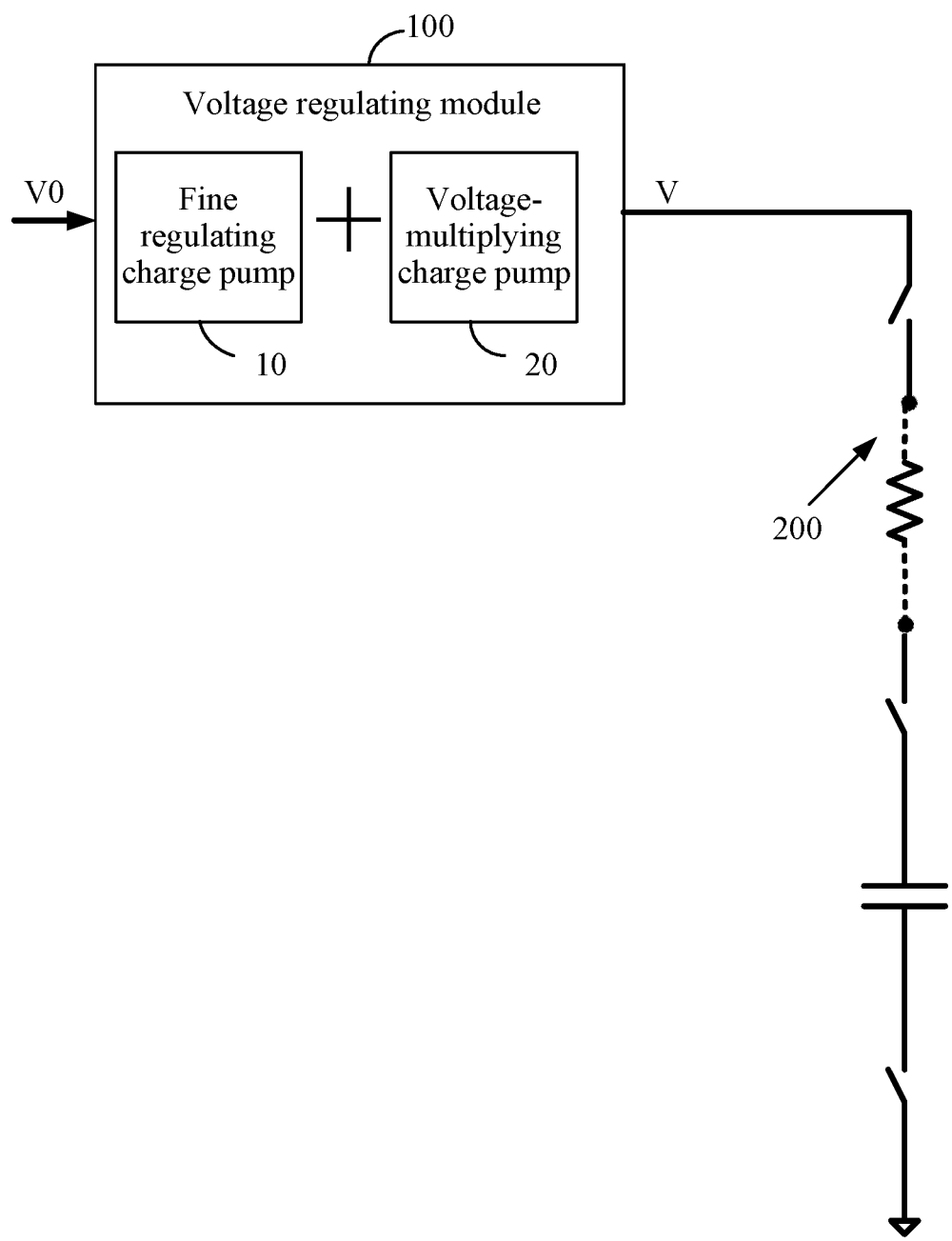
FIG. 2 is a schematic diagram of a voltage regulating module and a stimulation electrode according to an embodiment of the present disclosure.

In conjunction with FIG. 2, the implantable nerve stimulation system further includes a voltage regulating module 100. The voltage regulating module 100 may be disposed in, but is not limited to, the terminal device 600.

The voltage regulating module 100 is configured to output a total output voltage V to control the electrical stimulation amplitude of the stimulation electrode 200.

In this embodiment, the voltage regulating module 100 includes a fine regulating charge pump 10 and a voltage-multiplying charge pump 20 connected to each other.

A first output voltage of the fine regulating charge pump 10 is $V_1 = m * V_0$, a second output voltage of the voltage-multiplying charge pump is 20 $V_2 = n * V_0$, and a total output voltage of the voltage regulating module 100 is $V = V_1 + V_2$. $V_0$ is an input voltage, a value of m ranges from 0 to 1, and n is an integer greater than or equal to 1.

It is to be noted that the input voltage $V_0$ is a power supply voltage provided by the battery, but it is not limited thereto.

In this embodiment, the combination mode of the fine regulating charge pump 10 and the voltage-multiplying charge pump 20 outputs a large-scale finely-regulatable total output voltage V, so that the actual total output voltage V is close to a required stimulation amplitude as much as possible, thereby greatly reducing power consumption.

Figure 3:
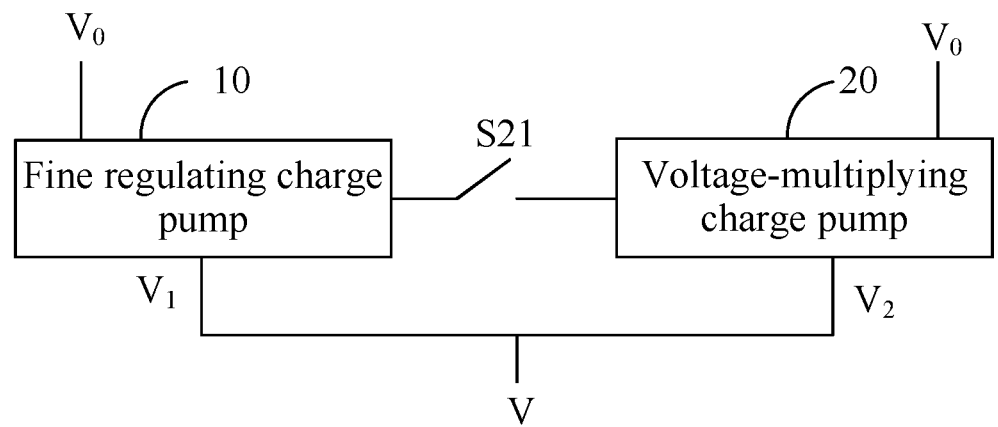
FIG. 3 is a block diagram of a voltage regulating module according to an embodiment of the present disclosure.

In this embodiment, referring to FIG. 3, an input terminal of the fine regulating charge pump is connected to the input voltage $V_0$, an input terminal of the voltage-multiplying charge pump 20 is connected to the input voltage $V_0$, and the fine regulating charge pump 10 and the voltage-multiplying charge pump 20 are connected through an intermediate switch S21.

It can be seen that the input voltage $V_0$ is input by the fine regulating charge pump 10 and the voltage-multiplying charge pump 20 separately. When the intermediate switch S21 is turned on, the fine regulating charge pump 10 and the voltage-multiplying charge pump 20 are connected in series with each other, the total output voltage V of the voltage regulating module 1 is a sum of the first output voltage $V_1$ and the second output voltage $V_2$. Theoretically, the total output voltage V may be equal to the first output voltage $V_1$ or the second output voltage $V_2$. In this embodiment, the case where an output terminal of the total output voltage V is located at the charge pump 20 and the total output voltage V is the sum of the first output voltage $V_1$ and the second output voltage $V_2$ is taken as an example.

Hereinafter, the specific circuit diagram of the fine regulating charge pump 10 and the voltage-multiplying charge pump 20 are introduced in detail.

Figure 4:
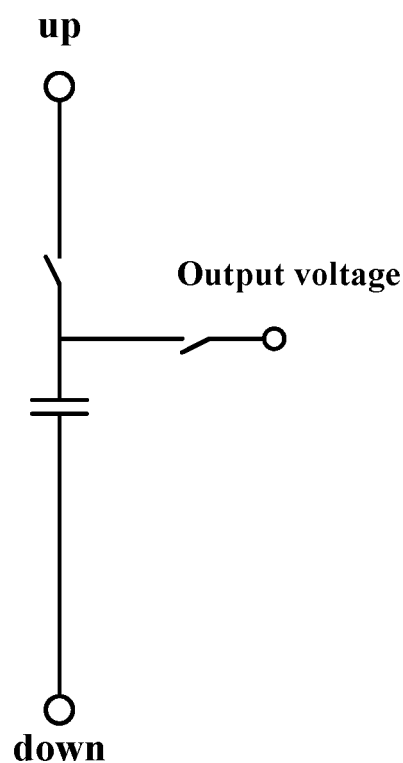
FIG. 4 is a circuit diagram of basic components of a fine regulating charge pump according to an embodiment of the present disclosure.
Figure 5:
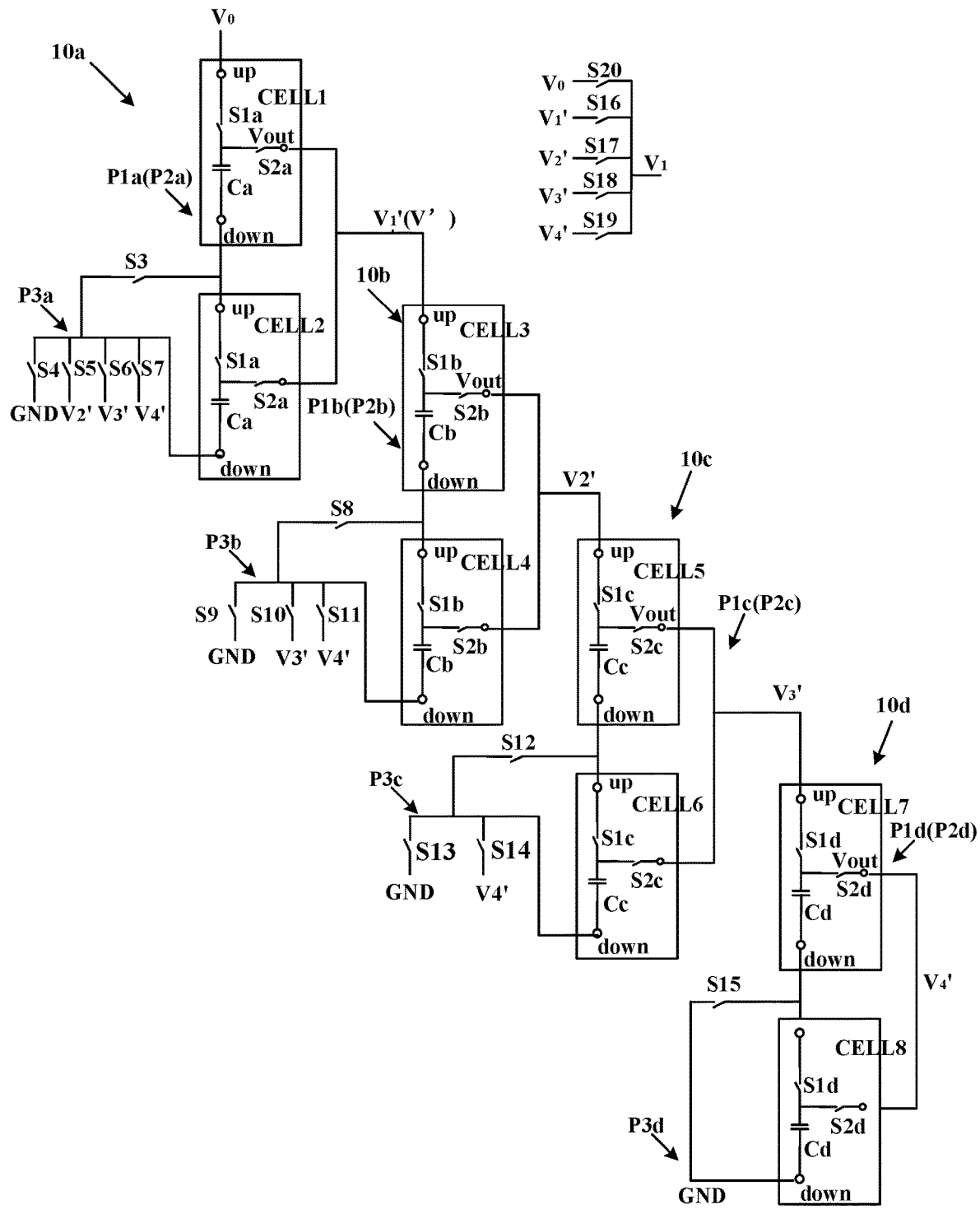
FIG. 5 is a circuit diagram of a fine regulating charge pump according to an embodiment of the present disclosure.

Referring to FIGS. 4 and 5, the fine regulating charge pump 10 includes several fine regulating charge pump basic units (10*a*, 10*b*, 10*c* and 10*d*).

Each fine regulating charge pump basic unit includes fine regulating charge branches (P1*a*, P1*b*, P1*c*, P1*d*), fine regulating discharge branches (P2*a*, P2*b*, P2*c*, P2*d*), several fine regulating capacitors (Ca, Cb, Cc, Cd) located in the fine regulating charge branches and the fine regulating discharge branches, and several fine regulating switches (S1*a*, S2*a*, S1*b*, S2*b*, S1*c*, S2*c*, S1*d*, S2*d*). The fine regulating charge branch is configured to charge several fine regulating capacitors. The fine regulating discharge branch is configured to output an intermediate output voltage V', the intermediate output voltage V' serves as the first output voltage V or is output to another adjacent fine regulating charge pump basic unit. The fine regulating charge branch and the fine regulating discharge branch are controlled by the several fine regulating switches to output different intermediate output voltages V'.

That is to say, at present, the intermediate output voltage V' output by the fine regulating charge pump basic unit may be directly output as the first output voltage V, and may also serve as the input voltage of another adjacent fine regulating charge pump basic unit, so that the first output voltages $V_1$ having different magnitudes may be output by multiple fine regulating charge pump basic units according to the requirements, and the first output voltage is $V_1=m*V_0$ and m ranges from 0 to 1.

Here, the case where each fine regulating charge pump basic unit includes two basic components (Cell 1 to Cell 8) is taken as an example. Referring to FIG. 4, each basic component includes two switches and a capacitor.

Each fine regulating charge pump basic unit further includes a series branch (P3a, P3b, P3c, P3d, a series branch voltage is marked as $V_3$, but not marked in the figure) connected in series with the fine regulating discharge branch, the series branch includes at least one series input terminal and a series switch (S3 to S15) for controlling opening and closing of the at least one series input terminal, the at least one series input terminal is configured to ground or connect the intermediate output voltage of another fine regulating charge pump basic unit to output a series voltage $V_3$, in a case where the fine regulating discharge branch and the series branch are turned on, the first output voltage $V_1$ is a sum of the intermediate output voltage V' of the fine regulating discharge branch and the series voltage $V_3$.

Each fine regulating charge pump basic unit includes two fine regulating capacitors. In a case where the fine regulating charge branch is turned on, the input voltage $V_0$ or the intermediate output voltage V' charges the two fine regulating capacitors connected in series, and in a case where the fine regulating discharge branch and the series branch are turned on, the two fine regulating capacitors are connected in parallel, the first output voltage $V_1$ is a sum of voltages at both ends of the fine regulating capacitors and the series voltage $V_3$.

In one specific example, referring to FIG. 5, the fine regulating charge pump 10 includes four fine regulating charge pump basic units, and each fine regulating charge pump basic unit includes two basic components, apparently, in other examples, the number and connection relationship of the fine regulating charge pump basic units and the basic components may be determined according to the actual situation.

The fine regulating charge pump 10 includes a first fine regulating charge pump basic unit 10a, a second fine regulating charge pump basic unit 10b, a third fine regulating charge pump basic unit 10c and a fourth fine regulating charge pump basic unit 10d which are connected in sequence.

The first fine regulating charge pump basic unit 10a includes a first series branch P3a, a first fine regulating charge branch P1a, a first fine regulating discharge branch P2a, two first fine regulating capacitors Ca located in the first fine regulating charge branch P1b and the first fine regulating discharge branch P2a, and several first fine regulating switches (S1a and S2a), and the first fine regulating charge branch P2a is connected to the input voltage $V_0$, the first fine regulating discharge branch P2a outputs a first intermediate output voltage $V_1'$.

The second fine regulating charge pump basic unit 10b includes a second series branch P3b, a second fine regulating charge branch P1b, a second fine regulating discharge branch P2b, two second fine regulating capacitors Cb located in the second fine regulating charge branch P1b and the second fine regulating discharge branch P2b, and several second fine regulating switches (S1b and S2b), the second fine regulating charge branch P1b is connected to the first intermediate output voltage $V_1'$, and the second fine regulating discharge branch P2b outputs a second intermediate output voltage $V_2'$.

The third fine regulating charge pump basic unit 10c includes a third series branch P3c, a third fine regulating charge branch P1c, a third fine regulating discharge branch P2c, two third fine regulating capacitors Cc located in the third fine regulating charge branch P1c and the third fine regulating discharge branch P2c, and several third fine regulating switches (S1c and S2c), the third fine regulating charge branch P1c is connected to the second intermediate output voltage $V_2'$, and the third fine regulating discharge branch P2c outputs a third intermediate output voltage $V_3'$.

The fourth fine regulating charge pump basic unit 10d includes a fourth series branch P3d, a fourth fine regulating charge branch P1d, a fourth fine regulating discharge branch P2d, two fourth fine regulating capacitors Cb located in the fourth fine regulating charge branch P1d and the fourth fine regulating discharge branch P2d, and several fourth fine regulating switches (S1d and S2d), the fourth fine regulating charge branch P1d is connected to the third intermediate output voltage $V_3'$, and the fourth fine regulating discharge branch P2d outputs a fourth intermediate output voltage $V_4'$.

The first series branch P3a is grounded or connected to one of the second intermediate output voltage $V_2'$, the third intermediate output voltage V and the fourth intermediate output voltage $V_4'$, the second series branch P3b is grounded or connected to one of the third intermediate output voltage $V_3'$ and the fourth intermediate output voltage $V_4'$, the third series branch P3c is grounded or connected to the fourth intermediate output voltage $V_4'$, and the fourth series branch P3d is grounded.

Here, the fine regulating charge pump 10 outputs different first output voltages by controlling the opening and closing of the several fine regulating switches (S1a, S2a, S1b, S2b, S1c, S2c, S1d, S2d) and several series switches (S3 to S15).

Hereinafter, the specific switch timings when the fine regulating charge pump 10 outputs several first output voltages $V_1$ is introduced.

Figure 6:
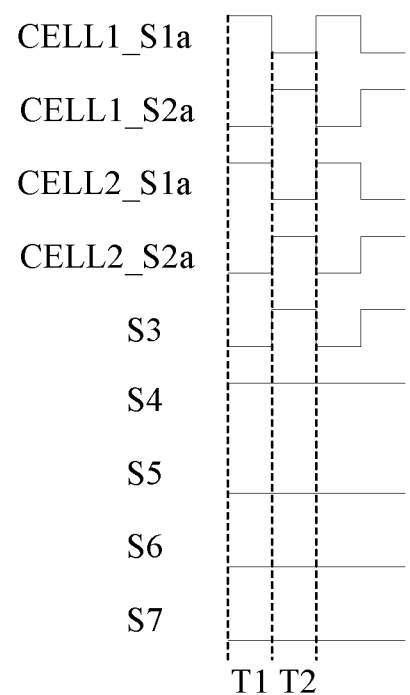
FIG. 6 is a switch timing diagram illustrating that a first output voltage is $V_1=\frac{1}{2}*V_0$ according to an embodiment of the present disclosure.

FIG. 6 is a switch timing diagram illustrating that a first output voltage is $V_1=\frac{1}{2}*V_0$. In this case, the first fine regulating charge pump basic unit 10a works.

In a first time period T1, the first fine regulating charge pump basic unit 10a enters a charging process.

The charging process of the first fine regulating charge pump basic unit 10a is that: first fine regulating switches S1a located in the basic component Cell1 and the basic component Cell2 of the first fine regulating charge branch P1a are both turned on (i.e., in a high level state), the first fine regulating switches S2a located in the basic component Cell1 and the basic component Cell2 of the first fine regulating discharge branch P2a are both turned off (i.e., in a low level state), and the series switch S4 is turned on and other series switches are turned off. That is to say, the first fine regulating charge branch P1a is turned on, the input voltage charges two first fine regulating capacitors Ca connected in series, and a voltage at both ends of each first fine regulating capacitor Ca is $\frac{1}{2}*V_0$.

In a second time period T2, the first fine regulating charge pump basic unit 10a enters a discharging process.

The discharging process of the first fine regulating charge pump basic unit 10a is that: the first fine regulating switches S1a located in the basic component Cell1 and the basic component Cell2 of the first fine regulating charge branch P1a are both turned off, the first fine regulating switches S2a located in the basic component Cell1 and the basic component Cell12 of the first fine regulating discharge branch P2a are both turned on, and the series switches S3 and S4 are turned on and other series switches are turned off. That is to say, the first series branch P3a is grounded, the first fine regulating discharge branch P2a is turned on, and the two first fine regulating capacitors Ca are connected in parallel, the first intermediate output voltage $V_1'$ is the voltage at both ends of each first fine regulating capacitor Ca, i.e., $V_1'=\frac{1}{2}*V_0$, and in this case, the first intermediate output voltage $V_1'$ is the first output voltage $V_1$ of the whole fine regulating charge pump 10, i.e., $V_1=\frac{1}{2}*V_0$.

Here, for ease of explanation, the switches S1a and S2a are referred to as the first fine regulating switches, and the switches S3 and S4 are referred to as the series switches. Reference can be made to the description here for the following description and repetition will not be made in this embodiment.

Figure 7:
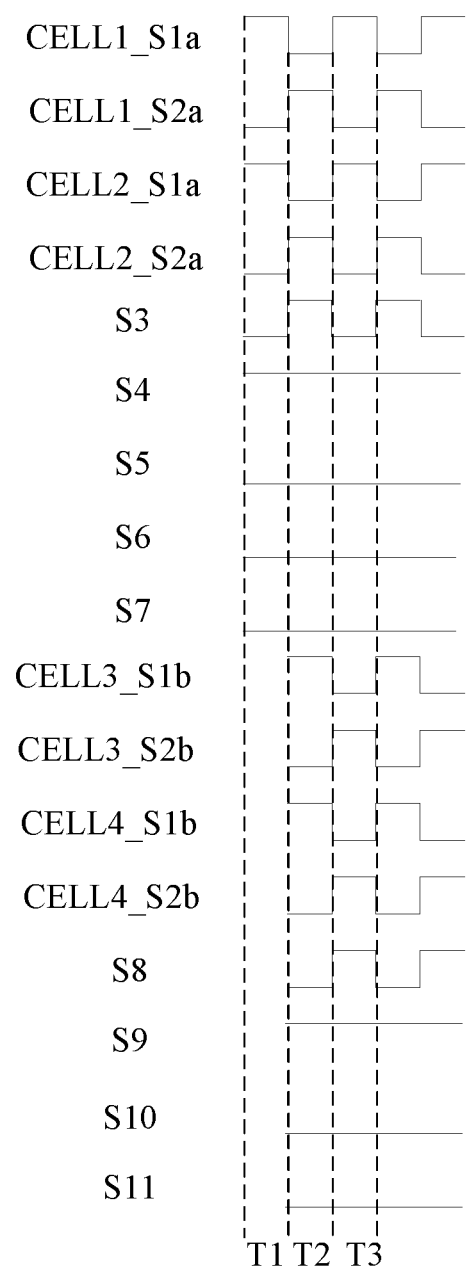
FIG. 7 is a switch timing diagram illustrating that a first output voltage is $V_1=\frac{1}{4}*V_0$ according to an embodiment of the present disclosure.

FIG. 7 is a switch timing diagram illustrating that a first output voltage is $V_1=\frac{1}{4}*V_0$. In this case, the first fine regulating charge pump basic unit 10a and the second fine regulating charge pump basic unit 10b works.

In a first time period T1, the first fine regulating charge pump basic unit 10a enters a charging process.

The charging process of the first fine regulating charge pump basic unit 10a is that: the first fine regulating switches S1a of the basic component Cell1 and the basic component Cell2 are both turned on, the first fine regulating switches S2a of the basic component Cell1 and the basic component Cell2 are both turned off, and the series switch S4 is turned on and other series switches are turned off. That is to say, the first fine regulating charge branch P1a is turned on, the input voltage charges two first fine regulating capacitors Ca connected in series, and a voltage at both ends of each first fine regulating capacitor Ca is $\frac{1}{2}*V_0$.

In a second time period T2, the first fine regulating charge pump basic unit 10a enters a discharging process, and at the same time, the second fine regulating charge pump basic unit 10b enters the charging process.

The discharging process of the first fine regulating charge pump basic unit 10a is that: the first fine regulating switches S1a of the basic component Cell1 and the basic component Cell2 are both turned off, the first fine regulating switches S2a of the basic component Cell1 and the basic component Cell2 are both turned on, and the series switches S3 and S4 are turned on and other series switches are turned off. That is to say, the first series branch P3a is grounded, the first fine regulating discharge branch P1a is turned on, and the two first fine regulating capacitors Ca are connected in parallel, the first intermediate output voltage $V_1'$ is the voltage at both ends of any one of the two first fine regulating capacitors Ca, i.e., $V_1'=\frac{1}{2}*V_0$, the first intermediate output voltage $V_1'$ is transmitted to the second fine regulating charge pump basic unit 10b.

The charging process of the second fine regulating charge pump basic unit 10b is that: the second fine regulating switches S1b of the basic component Cell3 and the basic component Cell4 are both turned on, the second fine regulating switches S2b of the basic component Cell3 and the basic component Cell4 are both turned off, and the series switch S9 is turned on and other series switches are turned off. That is to say, the second fine regulating charge branch P1b is turned on, the first intermediate output voltage $V_1'$ accessed to the second fine regulating charge pump basic unit 10b charges two second fine regulating capacitors Cb connected in series, and a voltage at both ends of each second fine regulating capacitor Cb is $\frac{1}{2}*V_1'$, i.e., $\frac{1}{4}*V_0$.

In a third time period T3, the first fine regulating charge pump basic unit 10a enters a charging process, and at the same time, the second fine regulating charge pump basic unit 10b enters the discharging process.

Here, the charging process of the first fine regulating charge pump basic unit 10a will not be described in detail.

The discharging process of the second fine regulating charge pump basic unit 10b is that: the second fine regulating switches S1b of the basic component Cell3 and the basic component Cell4 are both turned off, the second fine regulating switches S2b of the basic component Cell3 and the basic component Cell4 are both turned on, and the series switches S8 and S9 are turned on and other series switches are turned off. That is to say, the second series branch P3b is grounded, the second fine regulating discharge branch P2b is turned on, and the two second fine regulating capacitors Cb are connected in parallel, the first intermediate output voltage $V_2'$ is the voltage at both ends of any one of the two second fine regulating capacitors Cb, i.e., $V_2'=\frac{1}{4}*V_0$, and in this case, the second intermediate output voltage $V_2'$ is the first output voltage $V_1$ of the whole fine regulating charge pump 10, i.e., $V_1=\frac{1}{4}*V_0$.

Figure 8:
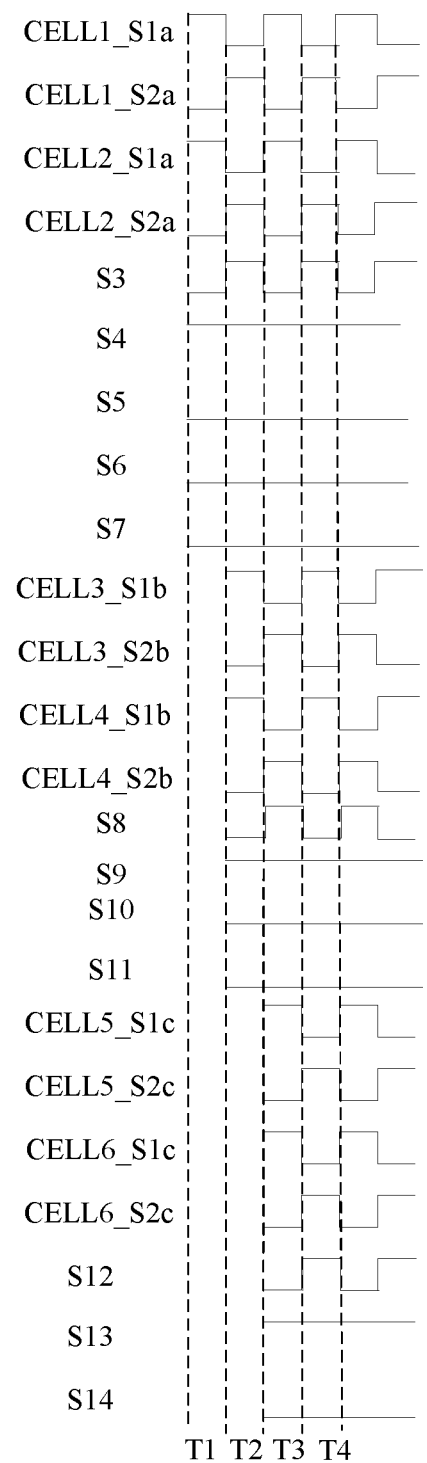
FIG. 8 is a switch timing diagram illustrating that a first output voltage is $V_1 = \frac{1}{8} * V_0$ according to an embodiment of the present disclosure.

FIG. 8 is a switch timing diagram illustrating that a first output voltage is $V_1=\frac{1}{8}*V_0$. In this case, the first fine regulating charge pump basic unit 10a, the second fine regulating charge pump basic unit 10b and the third fine regulating charge pump basic unit 10c works.

In a first time period T1, the first fine regulating charge pump basic unit 10a enters a charging process.

The charging process of the first fine regulating charge pump basic unit 10a is that: the first fine regulating switches S1a of the basic component Cell1 and the basic component Cell2 are both turned on, the first fine regulating switches S2a of the basic component Cell1 and the basic component Cell2 are both turned off, and the series switch S4 is turned on and other series switches are turned off. That is to say, the first fine regulating charge branch P1a is turned on, the input voltage charges two first fine regulating capacitors Ca connected in series, and a voltage at both ends of each first fine regulating capacitor Ca is $\frac{1}{2}*V_0$.

In a second time period T2, the first fine regulating charge pump basic unit 10a enters a discharging process and at the same time, the second fine regulating charge pump basic unit 10b enters the charging process.

The discharging process of the first fine regulating charge pump basic unit 10a is that: the first fine regulating switches S1a of the basic component Cell1 and the basic component Cell2 are both turned off, the first fine regulating switches S2a of the basic component Cell1 and the basic component Cell2 are both turned on, and the series switches S3 and S4 are turned on and other series switches are turned off. That is to say, the first series branch P3a is grounded, the first fine regulating discharge branch P1a is turned on, and the two first fine regulating capacitors Ca are connected in parallel, the first intermediate output voltage $V_1'$ is the voltage at both ends of any one of the two first fine regulating capacitors Ca, i.e., $V_1'=\frac{1}{2}*V_0$, the first intermediate output voltage $V_1'$ is transmitted to the second fine regulating charge pump basic unit 10b.

The charging process of the second fine regulating charge pump basic unit 10b is that: the second fine regulating switches S1b of the basic component Cell3 and the basic component Cell4 are both turned on, the second fine regulating switches S2b of the basic component Cell3 and the basic component Cell4 are both turned off, and the series switch S9 is turned on and other series switches are turned off. That is to say, the second fine regulating charge branch P1b is turned on, the first intermediate output voltage $V_1'$ accessed to the second fine regulating charge pump basic unit 10b charges two second fine regulating capacitors Cb connected in series, and a voltage at both ends of each second fine regulating capacitor Cb is $\frac{1}{2}*V_1'$, i.e., $\frac{1}{4}*V_0$.

In a third time period T3, the first fine regulating charge pump basic unit 10a enters the charging process, at the same time, the second fine regulating charge pump basic unit 10b enters the discharging process and the third fine regulating charge pump basic unit 10c enters the charging process.

Here, the charging process of the first fine regulating charge pump basic unit 10a will not be described in detail.

The discharging process of the second fine regulating charge pump basic unit 10b is that: the second fine regulating switches S1b of the basic component Cell3 and the basic component Cell4 are both turned off, the second fine regulating switches S2b of the basic component Cell3 and the basic component Cell4 are both turned on, and the series switches S8 and S9 are turned on and other series switches are turned off. That is to say, the second series branch P3b is grounded, the second fine regulating discharge branch P2b is turned on, and the two second fine regulating capacitors Cb are connected in parallel, the second intermediate output voltage $V_2'$ is the voltage at both ends of any one of the two second fine regulating capacitors Cb, i.e., $V_2'=\frac{1}{4}*V_0$, the second intermediate output voltage $V_2'$ is transmitted to the third fine regulating charge pump basic unit 10c.

The charging process of the third fine regulating charge pump basic unit 10c is that: the third fine regulating switches S1c of the basic component Cell5 and the basic component Cell6 are both turned on, the third fine regulating switches S2c of the basic component Cell5 and the basic component Cell6 are both turned off, and the series switch S13 is turned on and other series switches are turned off. That is to say, the third fine regulating charge branch P1c is turned on, the second intermediate output voltage $V_2'$ accessed to the third fine regulating charge pump basic unit 10c charges two third fine regulating capacitors Cc connected in series, and a voltage at both ends of each third fine regulating capacitor Cc is $\frac{1}{2}*V_2'$, i.e., $\frac{1}{8}*V_0$.

In a fourth time period T4, the first fine regulating charge pump basic unit 10a enters the discharging process, at the same time, the second fine regulating charge pump basic unit 10b enters the charging process and the third fine regulating charge pump basic unit 10c enters the discharging process.

Here, the discharging process of the first fine regulating charge pump basic unit 10a and the charging process of the second fine regulating charge pump basic unit 10b will not be described in detail.

The discharging process of the third fine regulating charge pump basic unit 10c is that: the third fine regulating switches S1c of the basic component Cell5 and the basic component Cell6 are both turned off, the third fine regulating switches S2c of the basic component Cell5 and the basic component Cell6 are both turned on, and the series switches S12 and S13 are turned on and other series switches are turned off. That is to say, the third series branch P3c is grounded, the third fine regulating discharge branch P2c is turned on, and the two third fine regulating capacitors Cc are connected in parallel, the third intermediate output voltage $V_3'$ is the voltage at both ends of any one of the two third fine regulating capacitors Cc, i.e., $V_3'=\frac{1}{8}*V_0$, and in this case, the third intermediate output voltage $V_3'$ is the first output voltage $V_1$ of the whole fine regulating charge pump 10, i.e., $V_1=\frac{1}{8}*V_0$.

Figure 9:
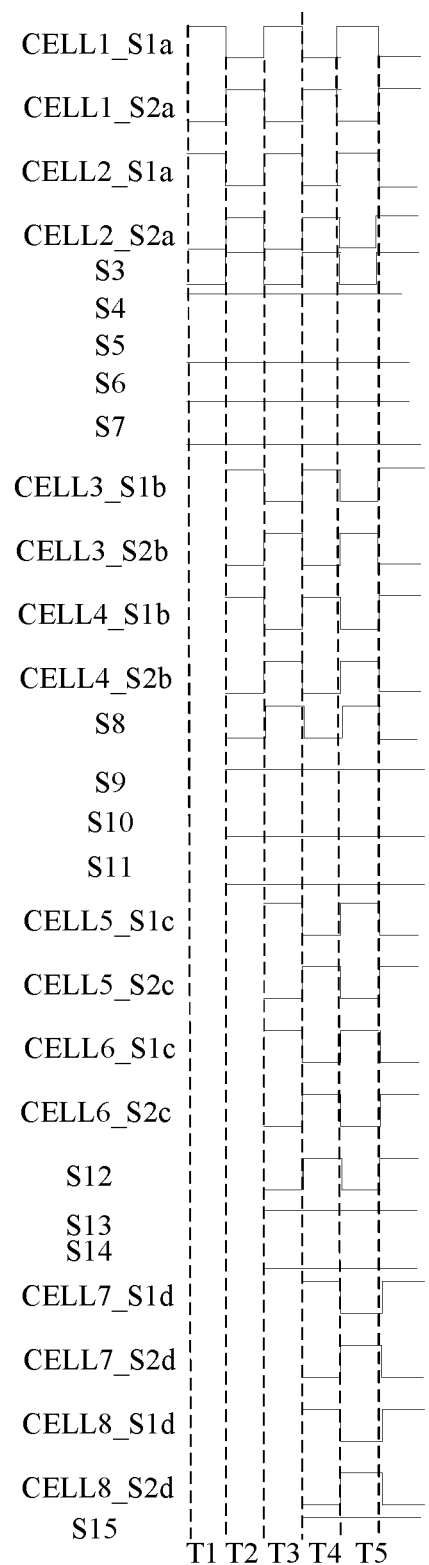
FIG. 9 is a switch timing diagram illustrating that a first output voltage is $V_1 = \frac{1}{16} * V_0$ according to an embodiment of the present disclosure.

FIG. 9 is a switch timing diagram illustrating that a first output voltage is $V_1=\frac{1}{16}*V_0$. In this case, the first fine regulating charge pump basic unit 10a, the second fine regulating charge pump basic unit 10b, the third fine regulating charge pump basic unit 10c and the fourth fine regulating charge pump basic unit 10d all work.

In a first time period T1, the first fine regulating charge pump basic unit 10a enters a charging process.

The charging process of the first fine regulating charge pump basic unit 10a is that: the first fine regulating switches S1a of the basic component Cell1 and the basic component Cell2 are both turned on, the first fine regulating switches S2a of the basic component Cell1 and the basic component Cell2 are both turned off, and the series switch S4 is turned on and other series switches are turned off. That is to say, the first fine regulating charge branch P1a is turned on, the input voltage $V_0$ charges two first fine regulating capacitors Ca connected in series, and a voltage at both ends of each first fine regulating capacitor Ca is $\frac{1}{2}*V_0$.

In a second time period T2, the first fine regulating charge pump basic unit 10a enters a discharging process, and at the same time, the second fine regulating charge pump basic unit 10b enters the charging process.

The discharging process of the first fine regulating charge pump basic unit 10a is that: the first fine regulating switches S1a of the basic component Cell1 and the basic component Cell2 are both turned off, the first fine regulating switches S2a of the basic component Cell1 and the basic component Cell2 are both turned on, and the series switches S3 and S4 are turned on and other series switches are turned off. That is to say, the first series branch P3a is grounded, the first fine regulating discharge branch P1a is turned on, and the two first fine regulating capacitors Ca are connected in parallel, the first intermediate output voltage $V_1'$ is the voltage at both ends of any one of the two first fine regulating capacitors Ca, i.e., $V_1'=\frac{1}{2}*V_0$, the first intermediate output voltage V1' is transmitted to the second fine regulating charge pump basic unit 10b.

The charging process of the second fine regulating charge pump basic unit 10b is that: the second fine regulating switches S1b of the basic component Cell3 and the basic component Cell4 are both turned on, the second fine regulating switches S2b of the basic component Cell3 and the basic component Cell4 are both turned off, and the series switch S9 is turned on and other series switches are turned off. That is to say, the second fine regulating charge branch P1b is turned on, the first intermediate output voltage $V_1'$ accessed to the second fine regulating charge pump basic unit 10b charges two second fine regulating capacitors Cb connected in series, and a voltage at both ends of each second fine regulating capacitor Cb is $\frac{1}{2}*V_1'$, i.e., $\frac{1}{4}*V_0$.

In a third time period T3, the first fine regulating charge pump basic unit 10a enters the charging process, at the same time, the second fine regulating charge pump basic unit 10b enters the discharging process and the third fine regulating charge pump basic unit 10c enters the charging process.

Here, the charging process of the first fine regulating charge pump basic unit 10a will not be described in detail.

The discharging process of the second fine regulating charge pump basic unit 10b is that: the second fine regulating switches S1b of the basic component Cell3 and the basic component Cell4 are both turned off, the second fine regulating switches S2b of the basic component Cell3 and the basic component Cell4 are both turned on, and the series switches S8 and S9 are turned on and other series switches are turned off. That is to say, the second series branch P3b is grounded, the second fine regulating discharge branch P2b is turned on, and the two second fine regulating capacitors Cb are connected in parallel, the second intermediate output voltage $V_2'$ is the voltage at both ends of any one of the two second fine regulating capacitors Cb, i.e., $V_2'=\frac{1}{4}*V_0$, the second intermediate output voltage $V_2'$ is transmitted to the third fine regulating charge pump basic unit 10c.

The charging process of the third fine regulating charge pump basic unit 10c is that: the third fine regulating switches S1c of the basic component Cell5 and the basic component Cell6 are both turned off, the third fine regulating switches S2c of the basic component Cell5 and the basic component Cell6 are both turned on, and the series switch S13 is turned on and other series switches are turned off. That is to say, the third fine regulating charge branch P1c is turned on, the second intermediate output voltage $V_2'$ accessed to the third fine regulating charge pump basic unit 10c charges two third fine regulating capacitors Cc connected in series, and a voltage at both ends of each third fine regulating capacitor Cc is $½*V_2'$, i.e., $⅛*V_0$.

In a fourth time period T4, the first fine regulating charge pump basic unit 10a enters the discharging process, at the same time, the second fine regulating charge pump basic unit 10b enters the charging process, the third fine regulating charge pump basic unit 10c enters the discharging process and the fourth fine regulating charge pump basic unit 10d enters the charging process.

Here, the discharging process of the first fine regulating charge pump basic unit 10a and the charging process of the second fine regulating charge pump basic unit 10b will not be described in detail.

The discharging process of the third fine regulating charge pump basic unit 10c is that: the third fine regulating switches S1c of the basic component Cell5 and the basic component Cell6 are both turned off, the third fine regulating switches S2c of the basic component Cell5 and the basic component Cell6 are both turned on, and the series switches S12 and S13 are turned on and other series switches are turned off. That is to say, the third series branch P3c is grounded, the third fine regulating discharge branch P2c is turned on, and the two third fine regulating capacitors Cc are connected in parallel, the third intermediate output voltage $V_3'$ is the voltage at both ends of any one of the two third fine regulating capacitors Cc, i.e., $V_3'=⅛*V_0$, the third intermediate output voltage $V_3'$ is transmitted to the fourth fine regulating charge pump basic unit 10d.

The charging process of the fourth fine regulating charge pump basic unit 10d is that: the fourth fine regulating switches S1d of the basic component Cell7 and the basic component Cell8 are both turned off, the fourth fine regulating switches S1d of the basic component Cell7 and the basic component Cell8 are both turned off, the fourth fine regulating switches S2d of the basic component Cell7 and the basic component Cell8 are both turned off, and the series switch S15 is turned off. That is to say, the fourth fine regulating switches S1d is turned on, the third intermediate output voltage $V_3'$ accessed to the fourth fine regulating charge pump basic unit 10d charges two fourth fine regulating capacitors Cd connected in series, and a voltage at both ends of each fourth fine regulating capacitor Cd is $½*V_3'$, i.e., $1/16*V_0$.

In a fifth time period T5, the first fine regulating charge pump basic unit 10a enters the charging process, at the same time, the second fine regulating charge pump basic unit 10b enters the discharging process, the third fine regulating charge pump basic unit 10c enters the charging process and the fourth fine regulating charge pump basic unit 10d enters the discharging process.

Here, the charging process of the first fine regulating charge pump basic unit 10a, the discharging process of the second fine regulating charge pump basic unit 10b and the charging process of the third fine regulating charge pump basic unit 10c will not be described in detail.

The discharging process of the fourth fine regulating charge pump basic unit 10d is that: the fourth fine regulating switches S1d of the basic component Cell7 and the basic component Cell8 are both turned off, the fourth fine regulating switches S2d of the basic component Cell7 and the basic component Cell8 are both turned on, and the series switch S15 is turned on. That is to say, the fourth series branch P3b is grounded, the fourth fine regulating discharge branch P2d is turned on, and the two fourth fine regulating capacitors Cd are connected in parallel, the fourth intermediate output voltage $V_4'$ is the voltage at both ends of any one of the two fourth fine regulating capacitors Cd, i.e., $V_4'=1/16*V_0$, and in this case, the fourth intermediate output voltage $V_4'$ is the first output voltage $V_1$ of the whole fine regulating charge pump 10, i.e., $V_1=1/16*V_0$.

It can be seen that the first fine regulating charge pump basic unit 10a, the second fine regulating charge pump basic unit 10b, the third fine regulating charge pump basic unit 10c and the fourth fine regulating charge pump basic unit 10d are selectively controlled to work to achieve different first output voltages $V_1$, and the first output voltages may be $½*V_0$, $¼*V_0$, $⅛*V_0$ and $1/16*V_0$.

Apparently, the first output voltage $V_1$ may also be other values, and the case where the first output voltage is $V_1=15/16*V_0$ is taken as an example for illustration.

Figure 10:
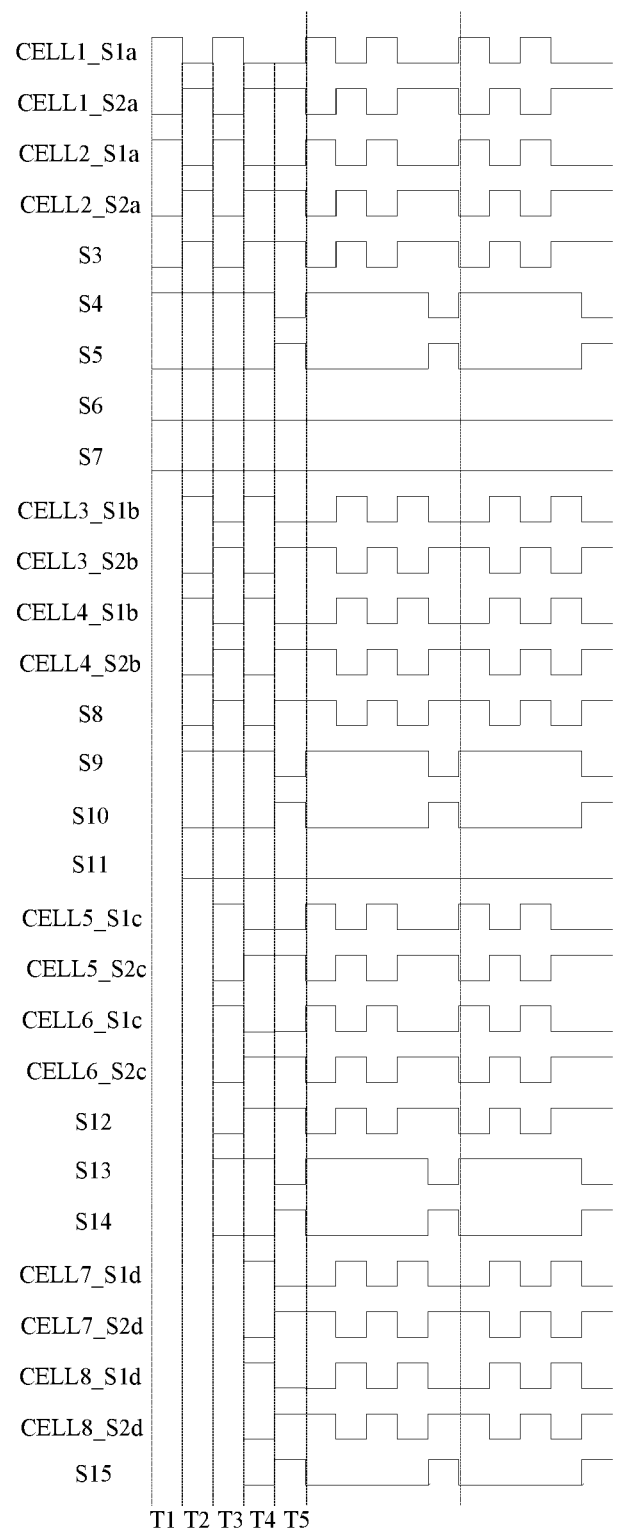
FIG. 10 is a switch timing diagram illustrating that a first output voltage is $V_1 = \frac{15}{16} * V_0$ according to an embodiment of the present disclosure.

FIG. 10 is a switch timing diagram illustrating that a first output voltage is $V_1=15/16*V_0$. In this case, the first fine regulating charge pump basic unit 10a, the second fine regulating charge pump basic unit 10b, the third fine regulating charge pump basic unit 10c and the fourth fine regulating charge pump basic unit 10d all work.

The difference between FIG. 10 and FIG. 9 lies in the fifth time period T5. Here, reference can be made to the description of FIG. 9 for the description of the first time period T1, the second time period T2, the third time period T3, and the fourth time period T4, which will not be repeated here.

In conjunction with FIG. 10, when in the fifth time period T5, the first fine regulating charge pump basic unit 10a, the second fine regulating charge pump basic unit 10b, the third fine regulating charge pump basic unit 10c and the fourth fine regulating charge pump basic unit 10d are all in the discharging process.

Here, the first series branch P3a includes a ground terminal GND, a second intermediate output voltage input terminal $V_2'$, a third intermediate output voltage input terminal $V_3'$, a fourth intermediate output voltage input terminal $V_4'$. The second series branch P3b includes the ground terminal GND, the third intermediate output voltage input terminal $V_3'$ and the fourth intermediate output voltage input terminal $V_4'$. The third series branch P3c includes the ground terminal GND and the fourth intermediate output voltage input terminal $V_4'$, and the fourth series branch P3d includes the ground terminal GND (in conjunction with FIG. 5).

When in the fifth time period T5, an output terminal of the fourth fine regulating charge pump basic unit 10d is connected to the fourth intermediate output voltage input terminal $V_4'$ of the third fine regulating charge pump basic unit 10c, an output terminal of the third fine regulating charge pump basic unit 10c is connected to the third intermediate output voltage input terminal $V_3'$ of the second fine regulating charge pump basic unit 10b, and an output terminal of the second fine regulating charge pump basic unit 10b is connected to the second intermediate output voltage input terminal $V_2'$ of the first fine regulating charge pump basic unit 10a.

In this case, when the output terminal of the fourth fine regulating charge pump basic unit 10d is connected to the fourth intermediate output voltage input terminal $V_4'$ of the third fine regulating charge pump basic unit 10c, and the series switches S14 and S12 are turned on, the third series branch P3c and the third fine regulating discharge branch P2c are connected in series. In this case, the third intermediate output voltage actually output by the third fine regulating charge pump basic unit 10c is $V_3' = \frac{1}{8}*V_0 + \frac{1}{16}*V_0$.

When the output terminal of the third fine regulating charge pump basic unit 10c is connected to the third intermediate output voltage input terminal $V_3'$ of the second fine regulating charge pump basic unit 10b, and the series switches S10 and S8 are turned on, the second series branch P3b and the second fine regulating discharge branch P2b are connected in series. In this case, the second intermediate output voltage actually output by the second fine regulating charge pump basic unit 10b is $V_2' = \frac{1}{4}*V_0 + \frac{1}{8}*V_0 + \frac{1}{16}*V_0$.

When the output terminal of the second fine regulating charge pump basic unit 10b is connected to the second intermediate output voltage input terminal $V_2'$ of the first fine regulating charge pump basic unit 10a, and the series switches S5 and S3 are turned on, The first series branch P3a and the first fine regulating discharge branch P2a are connected in series. In this case, the first intermediate output voltage actually output by the first fine regulating charge pump basic unit 10a is $V_1' = \frac{1}{2}*V_0 + \frac{1}{4}*V_0 + \frac{1}{8}*V_0 + \frac{1}{16}*V_0$, and in this case, the first intermediate output voltage $V_1'$ is the first output voltage of the whole fine regulating charge pump 10, i.e., $V_1 = \frac{1}{2}*V_0 + \frac{1}{4}*V_0 + \frac{1}{8}*V_0 + \frac{1}{16}*V_0 = \frac{15}{16}*V_0$.

Reference can be made to the description of FIG. 10 for the description of the first output voltage $V_1$ being the other values, and the output terminal of a specific fine regulating charge pump basic unit is selected to be connected to the series branch input terminal of a specific fine regulating charge pump basic unit, so that different first output voltages $V_1$ can be output.

For example, when in the fifth time period T5, the first fine regulating charge pump basic unit 10a, the second fine regulating charge pump basic unit 10b, the third fine regulating charge pump basic unit 10c and the fourth fine regulating charge pump basic unit 10d all work, the output terminal of the fourth fine regulating charge pump basic unit 10d is connected to the fourth intermediate output voltage input terminal $V_4'$ of the second fine regulating charge pump basic unit 10b, the output terminal of the second fine regulating charge pump basic unit 10b is connected to the second intermediate output voltage input terminal $V_2'$ of the first fine regulating charge pump basic unit 10a, an output terminal of the first fine regulating charge pump basic unit 10a serves as a final output terminal, and the first output voltage is $V_1 = \frac{1}{2}*V_0 + \frac{1}{4}*V_0 + \frac{1}{16}*V_0 = \frac{13}{16}*V_0$.

For another example, when in the fourth time period T4, the first fine regulating charge pump basic unit 10a, the second fine regulating charge pump basic unit 10b, the third fine regulating charge pump basic unit 10c all work, the output terminal of the third fine regulating charge pump basic unit 10c is connected to the third intermediate output voltage input terminal $V_3'$ of the second fine regulating charge pump basic unit 10b, the output terminal of the second fine regulating charge pump basic unit 10b serves as the final output terminal, and the first output voltage is $V_1 = \frac{1}{4}*V_0 + \frac{1}{8}*V_0 = \frac{6}{16}*V_0$.

Generally speaking, when the output terminal of the first fine regulating charge pump basic unit 10a serves as the final output terminal, the first output voltage $V_1$ may be $\frac{1}{2}*V_0$, $\frac{9}{16}*V_0$, $\frac{10}{16}*V_0$, $\frac{11}{16}*V_0$, $\frac{12}{16}*V_0$, $\frac{13}{16}*V_0$, $\frac{14}{16}*V_0$ and $\frac{15}{16}*V_0$, when the output terminal of the second fine regulating charge pump basic unit 10b serves as the final output terminal, the first output voltage $V_1$ may be $\frac{1}{4}*V_0$, $\frac{5}{16}*V_0$, $\frac{6}{16}*V_0$ and $\frac{7}{16}*V_0$, when the output terminal of the third fine regulating charge pump basic unit 10c serves as the final output terminal, the first output voltage $V_1$ may be $\frac{1}{8}*V_0$ and $\frac{3}{16}*V_0$, and when the output terminal of the fourth fine regulating charge pump basic unit 10d serves as the final output terminal, the first output voltage $V_1$ may be $\frac{1}{16}*V_0$.

In addition, the input voltage $V_0$ may also directly serve as the first output voltage $V_1$. Further, the fine regulating charge pump 10 also includes a control switch (S16 to S20) that controls the output of the first output voltage $V_1$. A control switch S16 is configured to control the output of the first fine regulating charge pump basic unit 10a, a control switch S17 is configured to control the output of the second fine regulating charge pump basic unit 10b, a control switch S18 is configured to control the output of the third fine regulating charge pump basic unit 10c, a control switch S19 is configured to control the output of the fourth fine regulating charge pump basic unit 10d, and the control switch S20 is configured to control the output of the input voltage $V_0$.

It can be seen that the output terminal of a specific fine regulating charge pump basic unit is selected to be connected to the series branch input terminal of a specific fine regulating charge pump basic unit, so that a value of the first output voltage $V_1$ ranges from $\frac{1}{16}*V_0$ to $V_0$, and a step size of the first output voltage $V_1$ is $\frac{1}{16}*V_0$.

Figure 11:
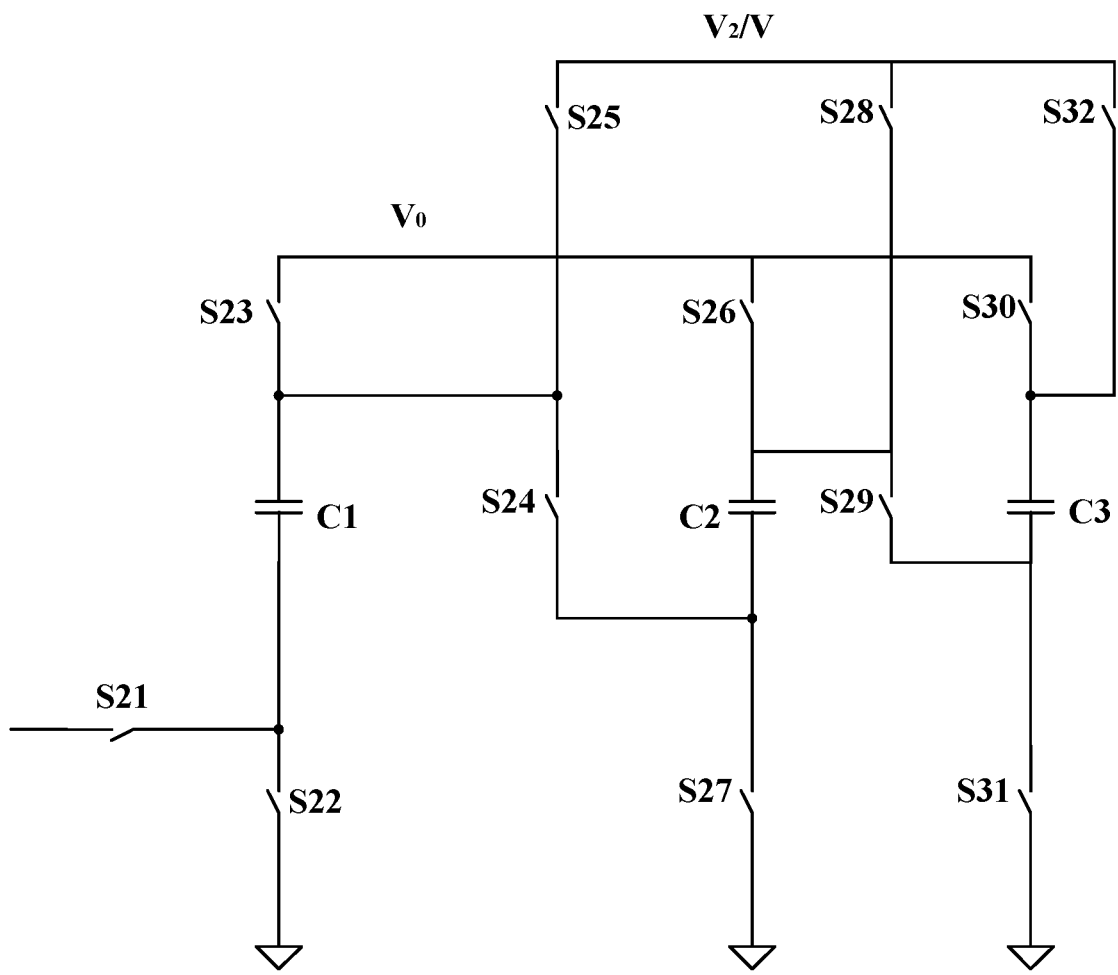
FIG. 11 is a circuit diagram of a voltage-multiplying charge pump according to an embodiment of the present disclosure.

FIG. 11 is a circuit diagram of a voltage-multiplying charge pump 20 according to an embodiment of the present disclosure.

The voltage-multiplying charge pump 20 includes: several voltage-multiplying charge branches, several voltage-multiplying discharge branches, several voltage-multiplying capacitors (C1, C2, C3) located in the several voltage-multiplying charge branches and the several voltage-multiplying discharge branches, and several voltage-multiplying charge switches (S22 to S32). The several voltage-multiplying charge branch is configured to charge the several voltage-multiplying capacitors, the several voltage-multiplying discharge branch is configured to output the second output voltage, and the several voltage-multiplying charge branches and the several voltage-multiplying discharge branches are controlled by the several voltage-multiplying switches to output different second output voltages $V_2$.

That is, different voltage-multiplying charge branches and voltage-multiplying discharge branches may be selected according to the requirements to output the first output voltage $V_2$ having different magnitudes, the second output voltage is $V_2 = n*V_0$, and N is an integer greater than or equal to 1.

In a specific example, the case where the voltage-multiplying charge pump 20 includes three voltage-multiplying charge branches, three voltage-multiplying discharge branches and three voltage-multiplying capacitors is taken as an example. Apparently, in other examples, the number and the connection relationship of the charge branches, the discharge branches and the voltage-multiplying capacitors of the voltage-multiplying charge pump 20 can be determined according to the actual situation.

The several voltage-multiplying charge branches include a first voltage-multiplying charge branch, a second voltage-multiplying charge branch and a third voltage-multiplying charge branch. The several voltage-multiplying discharge branches include a first voltage-multiplying discharge branch, a second voltage-multiplying discharge branch and a third voltage-multiplying discharge branch. The several voltage-multiplying capacitors include a first voltage-multiplying capacitor C1, a second voltage-multiplying capacitor C2 and a third voltage-multiplying capacitor C3.

The first voltage-multiplying charge branch is connected to the input voltage $V_0$ and the first voltage-multiplying capacitor C1, the second voltage-multiplying charge branch is connected to the input voltage $V_0$ and the second voltage-multiplying capacitor C2, the third voltage-multiplying charge branch is connected to the input voltage $V_0$ and the third voltage-multiplying capacitor C3, the first voltage-multiplying discharge branch is connected to the first voltage-multiplying capacitor C1, the second voltage-multiplying discharge branch is connected in series with the first voltage-multiplying capacitor C1 and the second voltage-multiplying capacitor C2, the third voltage-multiplying discharge branch is connected in series with the first voltage-multiplying capacitor C1, the second voltage-multiplying capacitor C2 and the third voltage-multiplying capacitor C3. When the first voltage-multiplying charge branch is turned on and then the first voltage-multiplying discharge branch is turned on, the second output voltage is $V_2=V_0$. When the first voltage-multiplying charge branch and the second voltage-multiplying charge branch are turned on and then the second voltage-multiplying discharge branch is turned on, the second output voltage is $V_2=2*V_0$. When the first voltage-multiplying charge branch, the second voltage-multiplying charge branch, the third voltage-multiplying charge branch are turned on and then the third voltage-multiplying discharge branch is turned on, the second output voltage is $V_2=3*V_0$.

Figure 12:
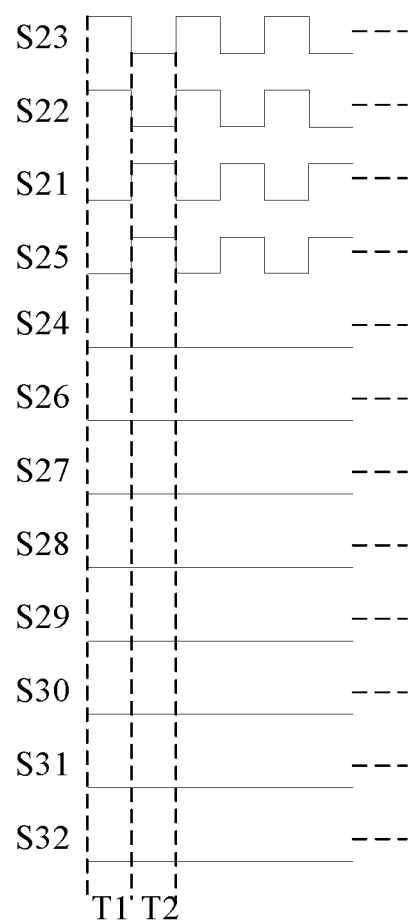
FIG. 12 is a switch timing diagram illustrating that a second output voltage is $V_2 = V_0$ according to an embodiment of the present disclosure.

Next, specific switch timings when the voltage-multiplying charge pump 20 outputs several different second output voltages $V_2$ are described FIG. 12 is a switch timing diagram illustrated that a second output voltage is $V_2=V_0$. In this case, the first voltage-multiplying charge branch and the first voltage-multiplying discharge branch work.

In a first time period T1, the first voltage-multiplying charge branch enters a charging process.

The charging process of the first voltage-multiplying charge branch is that: the voltage-multiplying switches S22 and S23 located in the first voltage-multiplying charge branch are all turned on, and the other voltage-multiplying switches and the intermediate switch S21 are turned off. That is to say, the first voltage-multiplying charge branch is turned on, the input voltage $V_0$ charges the first capacitor C1, and a voltage at both ends of the first capacitor C1 are $V_0$.

In a second time period T2, the first voltage-multiplying discharge branch enters a discharging process.

The discharging process of the first voltage-multiplying discharge branch is that: a voltage-multiplying switch S25 located in the first voltage-multiplying discharge branch and the intermediate switch S21 are all turned on, and the other voltage-multiplying switches are turned off. That is to say, the first voltage-multiplying discharge branch is turned on, the second output voltage is the voltage at both ends of the first capacitor C1, i.e., the second output voltage is $V_2=V_0$.

Here, for ease of illustration, each switch is referred to as the voltage-multiplying switch, and the intermediate switch S21 is also described here. Reference can be made to the description here for the following description and will not be described here.

Figure 13:
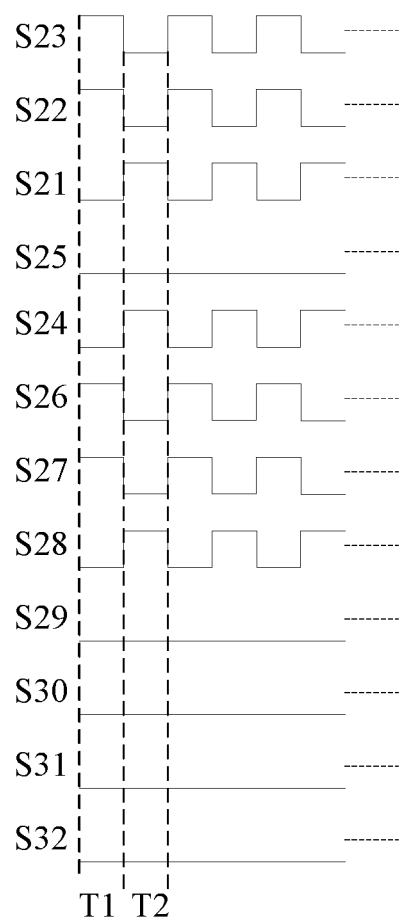
FIG. 13 is a switch timing diagram illustrating that a second output voltage is $V_2 = 2 * V_0$ according to an embodiment of the present disclosure.

FIG. 13 is a switch timing diagram illustrating that a second output voltage is $V_2=2*V_0$. In this case, the first voltage-multiplying charge branch, the second voltage-multiplying charge branch and the second voltage-multiplying discharge branch work.

In a first time period T1, the first voltage-multiplying charge branch and the second voltage-multiplying charge branch enters the charging process.

The charging process of the first voltage-multiplying charge branch and the second voltage-multiplying charge branch is that: the voltage-multiplying switches S22 and S23 located in the first voltage-multiplying charge branch are all turned on, the voltage-multiplying switches S26 and S27 located in the second voltage-multiplying charge branch are all turned on, and the other voltage-multiplying switches and the intermediate switch S21 are turned off. That is to say, the first voltage-multiplying charge branch and the second voltage-multiplying charge branch are turned on, the input voltage $V_0$ charges the first capacitor C1 and the second capacitor C2, and a voltage at both ends of the first capacitor C1 and a voltage at both ends of the second capacitor C2 are $V_0$.

In a second time period T2, the second voltage-multiplying discharge branch enters a discharging process.

The discharging process of the second voltage-multiplying discharge branch is that: the voltage-multiplying switches S24 and S28 located in the second voltage-multiplying discharge branch and the intermediate switch S21 are all turned on, and the other voltage-multiplying switches are turned off. That is to say, the second voltage-multiplying discharge branch is turned on, the first capacitor C1 is connected to the second capacitor C2 in series, the second output voltage $V_2$ is a sum of the voltage at both ends of the first capacitor C1 and a voltage at both ends of the second capacitor C2, i.e., the second output voltage is $V_2=2*V_0$.

Figure 14:
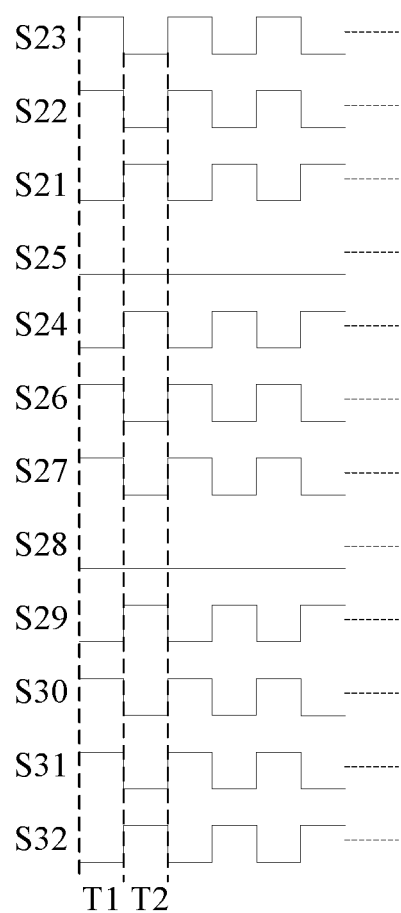
FIG. 14 is a switch timing diagram illustrating that a second output voltage is $V_2 = 3 * V_0$ according to an embodiment of the present disclosure.

FIG. 14 is a switch timing diagram illustrating that a second output voltage is $V_2=3*V_0$. In this case, the first voltage-multiplying charge branch, the second voltage-multiplying charge branch, the third voltage-multiplying charge branch and the third voltage-multiplying discharge branch work.

When in a first time period T1, the first voltage-multiplying charge branch, the second voltage-multiplying charge branch and the third voltage-multiplying charge branch enter a charging process.

The charging process of the first voltage-multiplying charge branch, the second voltage-multiplying charge branch and the third voltage-multiplying charge branch is that: the voltage-multiplying switches S22 and S23 located in the first voltage-multiplying charge branch are turned on, the voltage-multiplying switches S26 and S27 located in the second voltage-multiplying charge branch are turned on, the voltage-multiplying switches S30 and S31 located in the third voltage-multiplying charge branch are turned on, and the other voltage-multiplying switches and the intermediate switch S21 are turned off. That is to say, the first voltage-multiplying charge branch, the second voltage-multiplying charge branch and the third voltage-multiplying charge branch are turned on, and the input voltage $V_0$ charges the first capacitor C1, the second capacitor C2 and the third capacitor C3 separately, and the voltage at both ends of the first capacitor C1, the voltage at both ends of the second capacitor C2 and the voltage at both ends of the third capacitor C3 are all $V_0$.

When in a second time period T2, the third voltage-multiplying discharge branch enters a discharging process.

The discharging process of the third voltage-multiplying discharge branch is that: the voltage-multiplying switches S24, S29, S32 located in the third voltage-multiplying discharge branch and the intermediate switch S21 are turned on, and the other voltage-multiplying switches are turned off. That is to say, the third voltage-multiplying discharge branch is turned on, the first capacitor C1, the second capacitor C2 and the third capacitor C3 are connected in series, and the second output voltage $V_2$ is a sum of the voltage at both ends of the first capacitor C1, the voltage at both ends of the second capacitor C2 and the voltage at both ends of the third capacitor C3, i.e., the second output voltage is $V_2=3*V_0$.

It can be seen that by selecting a specific voltage-multiplying charge branch and a voltage-multiplying discharge branch, a value of the second output voltage ranges from $V_0$ to $3*V_0$ and a step size of the second output voltage is $V_0$.

Figure 15:
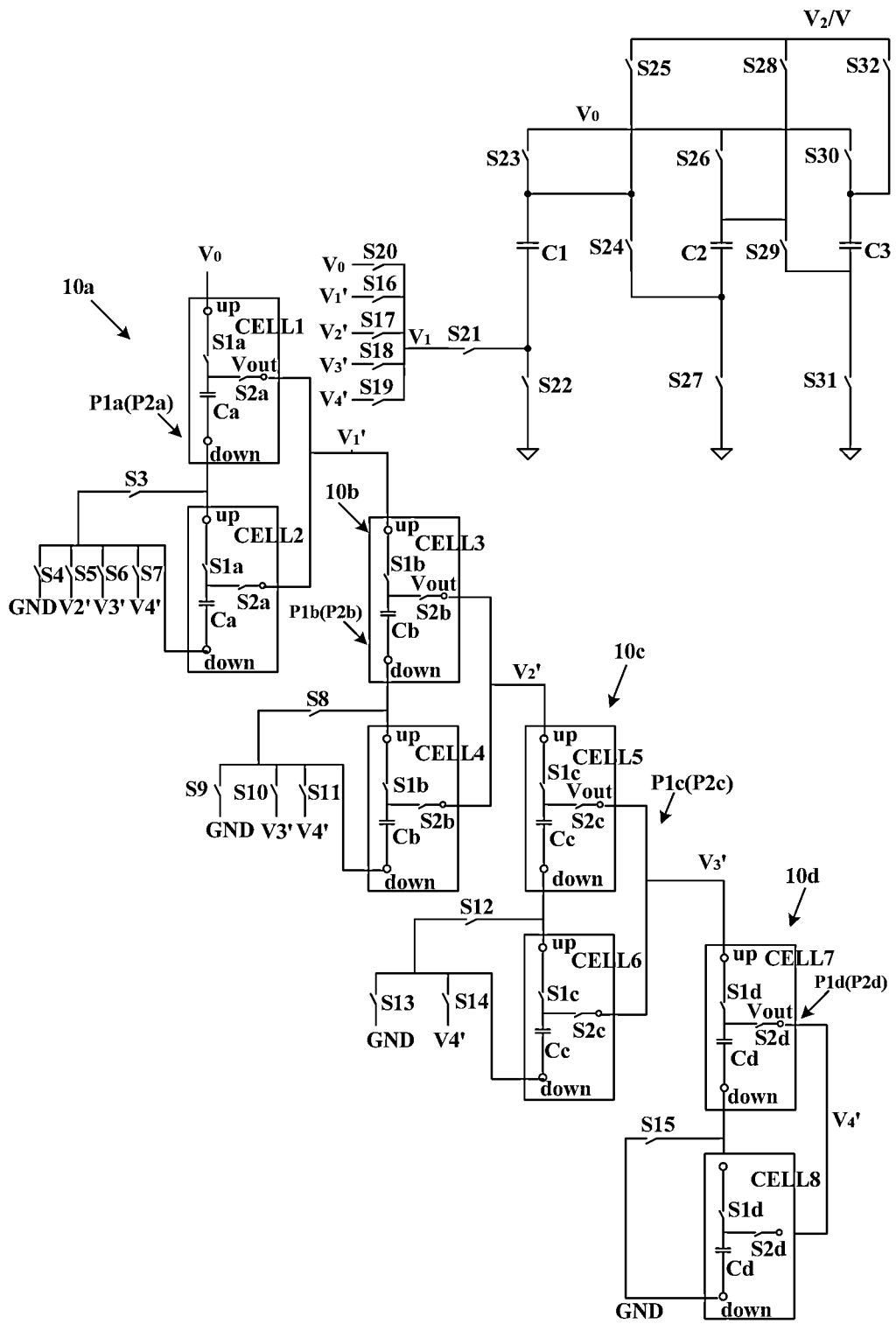
FIG. 15 is a circuit diagram of a voltage regulating module according to an embodiment of the present disclosure.

FIG. 15 is a circuit diagram of the whole voltage regulating module 100, which includes a fine regulating charge pump 10 and a voltage-multiplying charge pump 20 connected to each other.

When the intermediate switch S21 is turned on, the fine regulating charge pump 10 and the voltage-multiplying charge pump 20 are connected in series, the total output voltage V of the voltage regulating module 100 is a sum of the first output voltage $V_1$ and the second output voltage $V_2$, and values of the first output voltage $V_1$ and the second output voltage $V_2$ may be independently controlled, the control switches (S16 to S20) are controlled, so that the first output voltage $V_1$ having different values can be connected in series to the second output voltage $V_2$. The value of the total output voltage V of the voltage regulating module 100 ranges from $\frac{1}{16}*V_0$ to $4*V_0$, and the step size of the total output voltage V is $\frac{1}{16}*V_0$.

In this embodiment, the combination mode of the fine regulating charge pump 10 and the voltage-multiplying charge pump 20 generates a large-scale finely-regulatable output voltage while ensuring a high efficiency. In addition, a small number of capacitors are used in this embodiment, so that in a case where the load and frequency are matched, the efficiency can reach not less than 90%.

In addition, since the fine regulating charge pump 10 and the voltage-multiplying charge pump 20 work together, the fine regulating charge pump 10 and the voltage-multiplying charge pump 20 need to pay attention to the timing cooperation, and different timing relationships are required for different total output voltages V.

For example, when the total output voltage V is $3*V_0+\frac{15}{16}*V_0$, a period duration required by the voltage-multiplying charge pump 20 to output a second output voltage $V_2$ of $3*V_0$ is defined to be t, a period duration required by the fine regulating charge pump 10 to output a first output voltage $V_1$ of $\frac{5}{16}*V_0$ is 2.5t. Therefore, in order to match the period duration of the fine regulating charge pump 10 with the period duration of the voltage-multiplying charge pump 20, the period duration of the voltage-multiplying charge pump 20 needs to extend to 2.5 t. Therefore, a duty ratio of a high level of the voltage-multiplying charge pump 20 is not equal to 50%, apparently, the specific duty ratio of the high level and the low level can be determined according to the actual situation.

Figure 16:
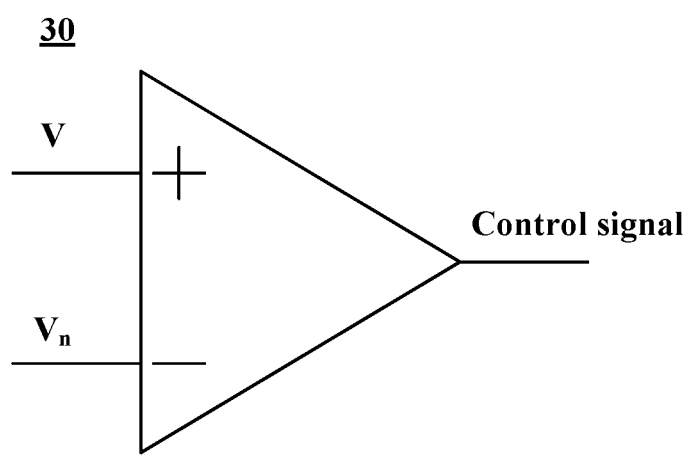
FIG. 16 is a schematic diagram of a comparator according to an embodiment of the present disclosure.

In this embodiment, in conjunction with FIG. 16, the total output voltage V of the voltage regulating module 100 is affected by the load, so the switch (including the fine regulating switch, the voltage-multiplying switch, the series switch and the like) frequency can be automatically adjusted by using the close-cycle control.

Here, the voltage regulating module 100 also includes a comparator 30, two input ends of the comparator 30 are respectively connected to a preset voltage $V_n$ and a total output voltage V, the total output voltage V is controlled by several switches, and in a case where the total output voltage V is not greater than the preset voltage $V_n$, the comparator 30 outputs a control signal to improve a working frequency of the several switches, thereby greatly improving the output frequency of the voltage regulating module 100.

In addition, if the switch frequency is raised to a maximum value and the preset voltage $V_n$ still cannot be reached, the input voltage is raised.

In summary, the present disclosure adopts the combination mode of the fine regulating charge pump 10 and the voltage-multiplying charge pump 20 to output a large-scale finely-regulatable total output voltage V, so that the actual output voltage V is close to a required stimulation amplitude as much as possible, thereby greatly reducing power consumption.

In addition, a small number of capacitors are used in this embodiment, so that in a case where the load and frequency are matched, the efficiency can reach more than 90%, and at the same time, the high efficiency can be ensured.

It is to be understood that although this specification is described in terms of the embodiments, not every embodiment includes only one independent technical solution. Such description mode of the specification is merely for the sake of clarity, and those skilled in the art should regard the specification as a whole. The technical solutions in the embodiments may also be appropriately combined to form other embodiments which are understood by those skilled in the art.

The series of detailed descriptions listed above are merely specific descriptions of feasible embodiments of the present disclosure and are not intended to limit the protection scope of the present disclosure. Any equivalent embodiments or variations made without departing from the technical spirit of the present disclosure should be included within the protection scope of the present disclosure.

The invention claimed is:

1. A voltage regulating module, comprising: a fine regulating charge pump and a voltage-multiplying charge pump connected to each other, wherein a first output voltage of the fine regulating charge pump is V1=m*V0, a second output voltage of the voltage-multiplying charge pump is V2=n*V0, and a total output voltage of the voltage regulating module is V=V1+V2, wherein V0 is an input voltage, a value of m ranges from 0 to 1, and n is an integer greater than or equal to 1; and
wherein the voltage regulating module further comprises a comparator, two input ends of the comparator are respectively connected to a preset voltage and the total output voltage, the total output voltage is controlled by a plurality of switches, and in a case where the total output voltage is not greater than the preset voltage, the comparator outputs a control signal to improve a working frequency of the plurality of switches.

2. The voltage regulating module of claim 1, wherein an input terminal of the fine regulating charge pump is connected to the input voltage, an input terminal of the voltage-multiplying charge pump is connected to the input voltage, and the fine regulating charge pump and the voltage-multiplying charge pump are connected through an intermediate switch.

3. The voltage regulating module of claim 1, wherein the fine regulating charge pump comprises: a plurality of fine regulating charge pump basic units, wherein each of the plurality of fine regulating charge pump basic units comprises a fine regulating charge branch, a fine regulating discharge branch, a plurality of fine regulating capacitors located in the fine regulating charge branch and the fine regulating discharge branch, and a plurality of fine regulating switches, wherein the fine regulating charge branch is configured to charge the plurality of fine regulating capacitors, the fine regulating discharge branch is configured to output an intermediate output voltage, the intermediate output voltage serves as a first output voltage or is output to another adjacent fine regulating charge pump basic unit, and the fine regulating charge branch and the fine regulating discharge branch are controlled by the plurality of fine regulating switches to output different intermediate output voltages.

4. The voltage regulating module of claim 3, each of the plurality of fine regulating charge pump basic units further comprises a series branch connected in series with the fine regulating discharge branch, the series branch comprises at least one series input terminal and a series switch for controlling opening and closing of the at least one series input terminal, the at least one series input terminal is configured to ground or connect the intermediate output voltage of another fine regulating charge pump basic unit to output a series voltage, in a case where the fine regulating discharge branch and the series branch are turned on, the first output voltage is a sum of the intermediate output voltage of the fine regulating discharge branch and the series voltage.

5. The voltage regulating module of claim 4, wherein each of the plurality of fine regulating charge pump basic units comprises two fine regulating capacitors, in a case where the fine regulating charge branch is turned on, the input voltage or the intermediate output voltage charges the two fine regulating capacitors connected in series, and then in a case where the fine regulating discharge branch and the series branch are turned on, the two fine regulating capacitors are connected in parallel, the first output voltage is a sum of voltages at both ends of the two fine regulating capacitors and the series voltage.

6. The voltage regulating module of claim 5, wherein the fine regulating charge pump comprises a first fine regulating charge pump basic unit, a second fine regulating charge pump basic unit, a third fine regulating charge pump basic unit and a fourth fine regulating charge pump basic unit which are connected in sequence, wherein the first fine regulating charge pump basic unit comprises a first series branch, a first fine regulating charge branch, a first fine regulating discharge branch, two first fine regulating capacitors located in the first fine regulating charge branch and the first fine regulating discharge branch, and a plurality of first fine regulating switches, and the first fine regulating charge branch is connected to the input voltage, the first fine regulating discharge branch outputs a first intermediate output voltage;

wherein the second fine regulating charge pump basic unit comprises a second series branch, a second fine regulating charge branch, a second fine regulating discharge branch, two second fine regulating capacitors located in the second fine regulating charge branch and the second fine regulating discharge branch, and a plurality of second fine regulating switches, the second fine regulating charge branch is connected to the first intermediate output voltage, and the second fine regulating discharge branch outputs a second intermediate output voltage;

wherein the third fine regulating charge pump basic unit comprises a third series branch, a third fine regulating charge branch, a third fine regulating discharge branch, two third fine regulating capacitors located in the third fine regulating charge branch and the third fine regulating discharge branch, and a plurality of third fine regulating switches, the third fine regulating charge branch is connected to the second intermediate output voltage, and the third fine regulating discharge branch outputs a third intermediate output voltage;

wherein the fourth fine regulating charge pump basic unit comprises a fourth series branch, a fourth fine regulating charge branch, a fourth fine regulating discharge branch, two fourth fine regulating capacitors located in the fourth fine regulating charge branch and the fourth fine regulating discharge branch, and a plurality of fourth fine regulating switches, the fourth fine regulating charge branch is connected to the third intermediate output voltage, and the fourth fine regulating discharge branch outputs a fourth intermediate output voltage, and wherein the first series branch is grounded or connected to one of the second intermediate output voltage, the third intermediate output voltage and the fourth intermediate output voltage, the second series branch is grounded or connected to one of the third intermediate output voltage and the fourth intermediate output voltage, the third series branch is grounded or connected to the fourth intermediate output voltage, and the fourth series branch is grounded.

7. The voltage regulating module of claim 1, wherein the voltage-multiplying charge pump comprises: a plurality of voltage-multiplying charge branches, a plurality of voltage-multiplying discharge branches, a plurality of voltage-multiplying capacitors located in the plurality of voltage-multiplying charge branches and the plurality of voltage-multiplying discharge branches, and a plurality of voltage-multiplying charge switches, wherein the plurality of voltage-multiplying charge branches are configured to charge the plurality of voltage-multiplying capacitors, the plurality of voltage-multiplying discharge branches are configured to output the second output voltage, and the plurality of voltage-multiplying charge branches and the plurality of voltage-multiplying discharge branches are controlled by the plurality of voltage-multiplying switches to output different second output voltages.

8. The voltage regulating module of claim 7, wherein the plurality of voltage-multiplying charge branches comprises a first voltage-multiplying charge branch, a second voltage-multiplying charge branch, and a third voltage-multiplying charge branch; the plurality of voltage-multiplying discharge branches comprises a first voltage-multiplying discharge branch, a second voltage-multiplying discharge branch, and a third voltage-multiplying discharge branch; and the plurality of voltage-multiplying capacitors comprise a first voltage-multiplying capacitor, a second voltage-multiplying capacitor, and a third voltage-multiplying capacitor, wherein the first voltage-multiplying charge branch is connected to the input voltage and the first voltage-multiplying capacitor, the second voltage-multiplying charge branch is connected to the input voltage and the second voltage-multiplying capacitor, and the third voltage-multiplying charge branch is connected to the input voltage and the third voltage-multiplying capacitor, wherein the first voltage-multiplying discharge branch is connected to the first voltage-multiplying capacitor, the second voltage-multiplying discharge branch is connected in series with the first voltage-multiplying capacitor and the second voltage-multiplying capacitor, and the third voltage-multiplying discharge branch is connected in series with the first voltage-multiplying capacitor, the second voltage-multiplying capacitor and the third voltage-multiplying capacitor, wherein in a case where the first voltage-multiplying charge branch is turned on and then the first voltage-multiplying discharge branch is turned on, the second output voltage V2=V0, wherein in a case where the first voltage-multiplying charge branch and the second voltage-multiplying charge branch are turned on and then the second voltage-multiplying discharge branch is turned on, the second output voltage V2=2*V0, and in a case where the first voltage-multiplying charge branch, the second voltage-multiplying charge branch and the third voltage-multiplying charge branch are turned on and then the third voltage-multiplying discharge branch is turned on, the second output voltage V2=3*V0.

9. An implantable nerve stimulation system, comprising a terminal device and a stimulation electrode, wherein the terminal device comprises the voltage regulating module of claim 1, and the voltage regulating module is configured to output the total output voltage to control an electrical stimulation amplitude of the stimulation electrode.

10. The implantable nerve stimulation system of claim 9, wherein an input terminal of the fine regulating charge pump is connected to the input voltage, an input terminal of the voltage-multiplying charge pump is connected to the input voltage, and the fine regulating charge pump and the voltage-multiplying charge pump are connected through an intermediate switch.

11. The implantable nerve stimulation system of claim 9, wherein the fine regulating charge pump comprises: a plurality of fine regulating charge pump basic units, each of the plurality of fine regulating charge pump basic units comprises a fine regulating charge branch, a fine regulating discharge branch, a plurality of fine regulating capacitors located in the fine regulating charge branch and the fine regulating discharge branch, and a plurality of fine regulating switches, wherein the fine regulating charge branch is configured to charge the plurality of fine regulating capacitors, the fine regulating discharge branch is configured to output an intermediate output voltage, the intermediate output voltage serves as a first output voltage or is output to another adjacent fine regulating charge pump basic unit, and the fine regulating charge branch and the fine regulating discharge branch are controlled by the plurality of fine regulating switches to output different intermediate output voltages.

12. The implantable nerve stimulation system of claim 11, each of the plurality of fine regulating charge pump basic units further comprises a series branch connected in series with the fine regulating discharge branch, the series branch comprises at least one series input terminal and a series switch for controlling opening and closing of the at least one series input terminal, the at least one series input terminal is configured to ground or connect the intermediate output voltage of another fine regulating charge pump basic unit to output a series voltage, in a case where the fine regulating discharge branch and the series branch are turned on, the first output voltage is a sum of the intermediate output voltage of the fine regulating discharge branch and the series voltage.

13. The implantable nerve stimulation system of claim 12, wherein each of the plurality of fine regulating charge pump basic units comprises two fine regulating capacitors, in a case where the fine regulating charge branch is turned on, the input voltage or the intermediate output voltage charges the two fine regulating capacitors connected in series, and then in a case where the fine regulating discharge branch and the series branch are turned on, the two fine regulating capacitors are connected in parallel, the first output voltage is a sum of voltages at both ends of the two fine regulating capacitors and the series voltage.

14. The implantable nerve stimulation system of claim 13, wherein the fine regulating charge pump comprises a first fine regulating charge pump basic unit, a second fine regulating charge pump basic unit, a third fine regulating charge pump basic unit and a fourth fine regulating charge pump basic unit which are connected in sequence, wherein the first fine regulating charge pump basic unit comprises a first series branch, a first fine regulating charge branch, a first fine regulating discharge branch, two first fine regulating capacitors located in the first fine regulating charge branch and the first fine regulating discharge branch, and a plurality of first fine regulating switches, and the first fine regulating charge branch is connected to the input voltage, the first fine regulating discharge branch outputs a first intermediate output voltage;

wherein the second fine regulating charge pump basic unit comprises a second series branch, a second fine regulating charge branch, a second fine regulating discharge branch, two second fine regulating capacitors located in the second fine regulating charge branch and the second fine regulating discharge branch, and a plurality of second fine regulating switches, the second fine regulating charge branch is connected to the first intermediate output voltage, and the second fine regulating discharge branch outputs a second intermediate output voltage; wherein the third fine regulating charge pump basic unit comprises a third series branch, a third fine regulating charge branch, a third fine regulating discharge branch, two third fine regulating capacitors located in the third fine regulating charge branch and the third fine regulating discharge branch, and a plurality of third fine regulating switches, the third fine regulating charge branch is connected to the second intermediate output voltage, and the third fine regulating discharge branch outputs a third intermediate output voltage;

wherein the fourth fine regulating charge pump basic unit comprises a fourth series branch, a fourth fine regulating charge branch, a fourth fine regulating discharge branch, two fourth fine regulating capacitors located in the fourth fine regulating charge branch and the fourth fine regulating discharge branch, and a plurality of fourth fine regulating switches, the fourth fine regulating charge branch is connected to the third intermediate output voltage, and the fourth fine regulating discharge branch outputs a fourth intermediate output voltage, and wherein the first series branch is grounded or connected to one of the second intermediate output voltage, the third intermediate output voltage and the fourth intermediate output voltage, the second series branch is grounded or connected to one of the third intermediate output voltage and the fourth intermediate output voltage, the third series branch is grounded or connected to the fourth intermediate output voltage, and the fourth series branch is grounded.

15. The implantable nerve stimulation system of claim 9, wherein the voltage-multiplying charge pump comprises: a plurality of voltage-multiplying charge branches, a plurality of voltage-multiplying discharge branches, a plurality of voltage-multiplying capacitors located in the plurality of voltage-multiplying charge branches and the plurality of voltage-multiplying discharge branches, and a plurality of voltage-multiplying charge switches, wherein the plurality of voltage-multiplying charge branches are configured to charge the plurality of voltage-multiplying capacitors, the plurality of voltage-multiplying discharge branches are configured to output the second output voltage, and the plurality of voltage-multiplying charge branches and the plurality of voltage-multiplying discharge branches are controlled by the plurality of voltage-multiplying switches to output different second output voltages.

16. The implantable nerve stimulation system of claim 15, wherein the plurality of voltage-multiplying charge branches comprises a first voltage-multiplying charge branch, a second voltage-multiplying charge branch, and a third voltage-multiplying charge branch;

the plurality of voltage-multiplying discharge branches comprises a first voltage-multiplying discharge branch, a second voltage-multiplying discharge branch, and a third voltage-multiplying discharge branch; and the plurality of voltage-multiplying capacitors comprise a first voltage-multiplying capacitor, a second voltage-multiplying capacitor, and a third voltage-multiplying capacitor, wherein the first voltage-multiplying charge branch is connected to the input voltage and the first voltage-multiplying capacitor, the second voltage-multiplying charge branch is connected to the input voltage and the second voltage-multiplying capacitor, and the third voltage-multiplying charge branch is connected to the input voltage and the third voltage-multiplying capacitor, wherein the first voltage-multiplying discharge branch is connected to the first voltage-multiplying capacitor, the second voltage-multiplying discharge branch is connected in series with the first voltage-multiplying capacitor and the second voltage-multiplying capacitor, and the third voltage-multiplying discharge branch is connected in series with the first voltage-multiplying capacitor, the second voltage-multiplying capacitor and the third voltage-multiplying capacitor, wherein in a case where the first voltage-multiplying charge branch is turned on and then the first voltage-multiplying discharge branch is turned on, the second output voltage $V2=V0$, wherein in a case where the first voltage-multiplying charge branch and the second voltage-multiplying charge branch are turned on and then the second voltage-multiplying discharge branch is turned on, the second output voltage $V2=2*V0$, and in a case where the first voltage-multiplying charge branch, the second voltage-multiplying charge branch and the third voltage-multiplying charge branch are turned on and then the third voltage-multiplying discharge branch is turned on, the second output voltage $V2=3*V0$.

* * * * *